United States Patent
Miyazawa et al.

(10) Patent No.: US 6,391,288 B1
(45) Date of Patent: May 21, 2002

(54) MICROCAPSULE AND METHOD OF MAKING THE SAME

(75) Inventors: Kazuyuki Miyazawa; Isamu Kaneda; Toshio Yanaki, all of Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/625,504

(22) Filed: Jul. 26, 2000

(30) Foreign Application Priority Data

| Jul. 27, 1999 | (JP) | ............................................ 11-212373 |
| Mar. 28, 2000 | (JP) | ....................................... 2000-089742 |
| Mar. 28, 2000 | (JP) | ....................................... 2000-089743 |
| Mar. 28, 2000 | (JP) | ....................................... 2000-089744 |
| Mar. 28, 2000 | (JP) | ....................................... 2000-089745 |

(51) Int. Cl.⁷ ............................. A61K 7/42; A61K 7/44; A61K 7/021; A61K 7/025; A61K 9/48

(52) U.S. Cl. ............................. 424/59; 424/60; 424/63; 424/64; 424/400; 424/401; 424/451; 424/455; 424/457; 424/463; 424/489; 424/490; 424/493; 514/844; 514/937

(58) Field of Search ................................. 424/400, 401, 424/451, 455, 457, 463, 489, 490, 493, 59, 60, 63, 64; 514/937, 844

(56) References Cited

U.S. PATENT DOCUMENTS

| 4,129,645 A | * | 12/1978 | Barnett et al. ................. 424/60 |
| 4,273,672 A | * | 6/1981 | Vassiliades ................. 252/316 |
| 4,276,312 A | * | 6/1981 | Merritt ........................ 426/96 |
| 4,878,775 A | * | 11/1989 | Norbury et al. ............. 401/132 |
| 4,895,725 A | * | 1/1990 | Kantor et al. ................ 454/455 |
| 5,004,595 A | * | 4/1991 | Cherukuri et al. ............ 424/48 |
| 5,089,269 A | * | 2/1992 | Noda et al. ................. 424/456 |
| 5,540,927 A | * | 7/1996 | Jason et al. ................. 424/408 |
| 5,576,064 A | | 11/1996 | Fructus |
| 5,648,095 A | * | 7/1997 | Illum et al. ................. 424/489 |
| 5,656,263 A | | 8/1997 | Fructus |
| 5,855,856 A | * | 1/1999 | Lee et al. ................... 264/4.32 |
| 5,985,177 A | | 11/1999 | Yoshida et al. |
| 6,048,520 A | * | 4/2000 | Hoshowski ............... 424/70.17 |
| 6,103,271 A | * | 8/2000 | Morrison et al. ........... 424/490 |

FOREIGN PATENT DOCUMENTS

| JP | 52-8271 | | 3/1977 |
| JP | 57-29213 | | 6/1982 |
| JP | 58-143831 | | 8/1983 |
| JP | 02-117610 | | 5/1990 |
| JP | 03287511 A | * | 12/1991 |
| JP | 05-097660 | | 4/1993 |
| JP | 7-529 | | 1/1995 |
| JP | 07-101844 | | 4/1995 |
| JP | 08-259451 | | 10/1996 |
| JP | 09-163963 | | 6/1997 |
| JP | 09-255562 | | 9/1997 |
| JP | 10-174861 | | 6/1998 |

* cited by examiner

*Primary Examiner*—Jose' G. Dees
*Assistant Examiner*—Marina Lamm
(74) *Attorney, Agent, or Firm*—Fei-Fei Chao; Venable

(57) ABSTRACT

A microcapsule of the present invention is characterized in that it encapsulate oil droplets having average particle size of 0.01 to 3 μm and its capsulating agent is a hydrophilic polymer gelling agent. The main component of the capsulating agent is preferably a hydrophilic polymer gelling agent which hardens by heating and cooling, and, in particular, agar or carrageenan. In the making method of the present invention, a microcapsule can be made efficiently due to no loss in the inner oil phase, and its particle size can easily be controlled. The microcapsule is excellent in shearing-resistance, store stability. Also, if the fracture strength of the microcapsule is within a specific range, a microcapsule which releasing characteristic of encapsulated oil droplets when applied is immediately-, gradually- or non-releasing can be obtained. Further, when such a hydrophilic microcapsule is coated, the contraction in air, dispersibility to various medium, and elusion of encapsulated components in medium can be also improved.

32 Claims, 1 Drawing Sheet

1: encapsulated oil droplets (inner oil phase)
2: microcapsule    3: outer oil phase though the stability of such emulsion is insufficient, whereby oil droplets tend to fuse together, thus increasing the size of oil droplets encapsulated within the microcapsule. In such a case, there has been a problem that the microcapsule diameter is required to increase in order to enhance the capsulating efficiency of encapsulated oil droplets.

MICROCAPSULE AND METHOD OF MAKING THE SAME

RELATED APPLICATIONS

This application claims the priority of Japanese Patent Application No. 11-212373 filed on Jul. 27, 1999, and Japanese Patent Application Nos. 2000-89742, 2000-89743, 2000-89744 and 2000-89745 filed on Mar. 28, 2000, which are incorporated herein by reference.

FIELD OF THE INVENTION

This invention is related to a microcapsule and, in particular, to improvement in stability, feel of use, releasing characteristics of the encapsulated oil droplets and dispersibility of the microcapsule.

BACKGROUND OF THE INVENTION

Microcapsules having oil droplets encapsulated within a capsule have been studied in such fields as foods, medicines, cosmetics, and the like. For example, there have been attempts to improve the stability of a drug in a product by compounding a microcapsule having the drug encapsulated therein.

Known as a method of making a microcapsule is one comprising the steps of: preparing an O/W emulsion from an oil phase to become an encapsulated oil droplet and a water phase containing a capsulating agent; shaping this emulsion into a fine particle; and forming a capsule. Its examples include: a method in which the O/W emulsion is further dispersed and emulsified into an outer oil phase so as to form an O/W/O emulsion, and its water phase is hardened so as to form a capsule; a spray-cooling method in which the O/W emulsion is hardened while being sprayed in air; a dripping method in which the O/W emulsion is dripped from a nozzle so as to be hardened in a gas or liquid; and the like.

In conventional emulsifying methods, however, it is difficult for the O/W emulsion to have an emulsified particle size of 1 μm or less. Even if an O/W emulsion having an emulsified particle size of 1 μm or less can be made, the stability of such emulsion is insufficient, whereby oil droplets tend to fuse together, thus increasing the size of oil droplets encapsulated within the microcapsule. In such a case, there has been a problem that the microcapsule diameter is required to increase in order to enhance the capsulating efficiency of encapsulated oil droplets.

In the method via an O/W/O emulsion in particular, the O/W emulsion is further dispersed and emulsified into the outer oil phase, whereby not only the fusion between the encapsulated oil droplets but also the unification between the encapsulated oil droplets and the outer oil phase is likely to occur. Therefore, it has been problematic in that temperature and stirring speed are restricted upon the O/W/O emulsification, the particle size of microcapsule is very hard to control, and the stability of resulting microcapsule is not sufficient. Also, it has been desired to suppress loss in the inner oil phase at the time of making.

Further, the stability of microcapsule when compounded with other base materials, its feel of use on skin, and releasing characteristics of encapsulated oil droplets are important. For example, a microcapsule is likely to be destroyed when added in a making step of products such as milky lotion and cream, which are obtained as being stirred at a high speed in a viscous medium. It has conventionally been very difficult to obtain a microcapsule which would not be destroyed in the step of making such products. Also, as for releasing characteristics of encapsulated oil droplets when applied as being spread on skin, microcapsules having respective releasing characteristics such as:

(1) immediately-releasing microcapsules which are destroyed without a sense of incompatibility and release encapsulated oil droplets therefrom rapidly;

(2) gradually-releasing microcapsules which release encapsulated oil droplets therefrom gradually; and (3) non-releasing microcapsules which maintain encapsulated oil droplets and does not release them therefrom are desired depending on various purposes.

Japanese Unexamined Patent Publication No. 9-255562 reports an O/W/O emulsion in which a hydrophilic polymer and an organophilic clay mineral are compounded with its water phase and outer oil phase, respectively. However, there have been cases where, when an O/W particle is taken out from this O/W/O emulsion or the O/W/O emulsion per se is compounded with other base materials so as to form a product, the capsule is destroyed due to mechanical shearing or changes in base compositions in the step of making the product. Also, taking out an O/W particle from this O/W/O emulsion has been problematic in that contraction or destruction occurs, and that its dispersibility is unfavorable when dispersed in base materials again.

SUMMARY OF THE INVENTION

In view of the above-mentioned problems of the prior art, it is an object of the present invention to provide a microcapsule which is not destroyed even when compounded with other base materials so as to form a product, and exhibits favorable storage stability and feel of use, whose encapsulated oil droplets are (1) released immediately, (2) released gradually, or (3) not released at all when applied on skin.

It is another object of the present invention to provide a microcapsule which does not contract in air and exhibits a favorable dispersibility to various medium, whereas the elution of its encapsulated components is low in the medium.

Still another object of the present invention is to provide a method of making a microcapsule which can make such a microcapsule easily and efficiently, and also can easily control the microcapsule particle size over a wide range.

As the result that the inventors have carried out studies in view of the above-mentioned problems of the prior art, it has been found that, if a hydrophilic polymer gelling agent, one which hardens by heating and cooling in particular, is used as a main gelling agent, a microcapsule which is not destroyed even when compounded with other base materials so as to form a product and has a favorable storage stability can be obtained. Also, it has been found that, if the fracture strength of the microcapsule is within a specific range, releasing characteristics of encapsulated oil droplets can be controlled over a range from immediately-releasing to non-releasing.

Further, it has been found that when the microcapsule based on a hydrophilic polymer gelling agent is coated, the contraction in air, dispersibility to various medium, and elusion of encapsulated components in medium can be also improved, thereby accomplishing the present invention.

Namely, a microcapsule in accordance with the present invention is one wherein an oil droplet having an average particle size of 0.01 to 3 μm is encapsulated and a capsulating agent is a hydrophilic polymer gelling agent.

In the present invention, it is preferable that a fracture strength of the microcapsule is at least 10 g/cm² but less than 500 g/cm². Such a microcapsule can release the encapsulated oil droplet therefrom immediately when applied on skin.

Also, in the present invention, it is preferable that a fracture strength of the microcapsule is at least 500 g/cm² but less than 2,000 g/m². Such a microcapsule can release the encapsulated oil droplet therefrom gradually when applied on skin.

Also, in the present invention, it is preferable that a fracture strength of the microcapsule is at least 2,000 g/cm² but 5,000 g/cm² or less. Such a microcapsule does not release the encapsulated oil droplet therefrom when applied on skin.

In the present invention, it is preferable that the capsulating agent comprises essentially a hydrophilic polymer gelling agent which hardens by heating and cooling.

Preferred hydrophilic polymer gelling agent is agar or carrageenan.

Also, in the present invention, it is preferable that the microcapsule comprises a hydrophilic nonionic surfactant and a water-soluble solvent.

A microcapsule oily dispersion in accordance with the present invention is one wherein said microcapsule is dispersed in an oil phase.

The microcapsule oily dispersion is preferably obtained by the steps of:
preparing an O/W emulsion from an inner oil phase and a water phase containing the hydrophilic polymer gelling agent;
preparing an O/W/O emulsion by dispersing and emulsifying the O/W emulsion into an outer oil phase; and hardening the water phase of the O/W/O emulsion.

Also, the O/W emulsion is preferably prepared by the steps of:
preparing an oil-in-water-soluble-solvent type emulsion by adding the inner oil phase to a water-soluble solvent containing a hydrophilic nonionic surfactant; and
adding an aqueous solution of the hydrophilic polymer gelling agent to the oil-in-water-soluble-solvent type emulsion.

In the present invention, the microcapsule obtained by eliminating the outer oil phase of said microcapsule oil dispersion is preferable.

In the present invention, it is preferable that the microcapsule comprises an oil-soluble drug therein.

Also, in the present invention, it is preferable that the microcapsule comprises an organic UV-absorbing agent therein.

A cosmetic preparation in accordance with the present invention comprises said microcapsule.

A solid cosmetic preparation in accordance with the present invention comprises said microcapsule.

A sunscreen cosmetic preparation in accordance with the present invention comprises said microcapsule comprising an organic UV-absorbing agent therein.

A coated microcapsule in accordance with the present invention is one wherein said microcapsule coated with a coating agent.

In the present invention, it is preferably that the coating agent is a lipophilic or amphiphilic coating agent and, more preferably, a hydrophobic polysaccharide.

Also, in the present invention, it is preferably that the coating agent is a hydrophilic coating agent.

A cosmetic preparation in accordance with the present invention comprises said coated microcapsule.

A method of making a microcapsule in accordance with the present invention comprises the steps of:
preparing an O/W emulsion from an inner oil phase and a water phase in which a hydrophilic polymer gelling agent hardening by heating and cooling has been dissolved with heating beforehand, at a hardening temperature of the gelling agent or higher, said O/W emulsion having an average particle size of 0.01 to 3 μm;
preparing an O/W/O emulsion by dispersing and emulsifying the O/W emulsion into an outer oil phase at the hardening temperature of the gelling agent or higher; and
hardening and capsulating the water phase by cooling the O/W/O emulsion to the hardening temperature of the gelling agent or lower.

In the method of the present invention, it is preferable that the step of preparing the O/W emulsion comprises the steps of:
preparing an oil-in-water-soluble-solvent type emulsion by adding the inner oil phase into a water-soluble solvent containing a hydrophilic nonionic surfactant; and
mixing, at the hardening temperature of the gelling agent or higher, the oil-in-water-soluble-solvent type emulsion with an aqueous solution in which the hydrophilic polymer gelling agent hardening by heating and cooling has been dissolved with heating beforehand.

In the method of present invention, it is preferable that a gel prepared from the water phase has a fracture strength of at least 10 g/cm² but less than 500 g/cm².

Also, in the method of present invention, it is preferable that a gel prepared from the water phase has a fracture strength of at least 500 g/cm² but less than 2,000 g/cm².

Also, in the method of present invention, it is preferable that a gel prepared from the water phase has a fracture strength of at least 2,000 g/cm² but 5,000 g/cm² or less.

BEST MODE FOR CARRYING OUT THE INVENTION

Figure 1:
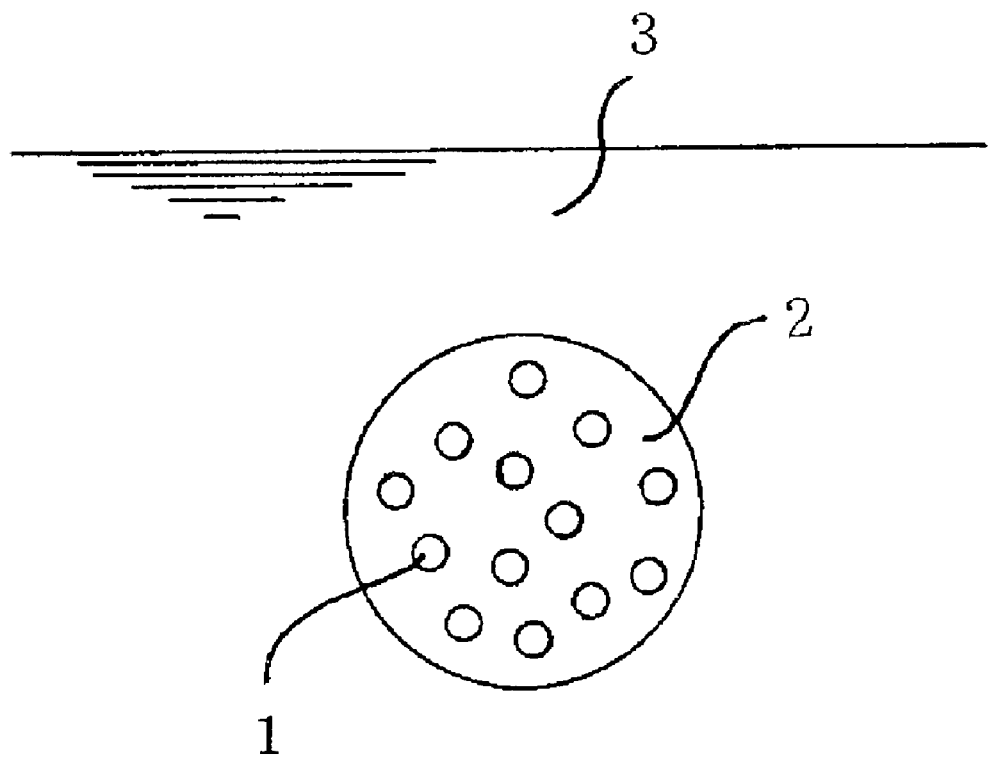
FIG. 1 is a conceptual view showing the microcapsule in accordance with the present invention.

The microcapsule of the present invention can be obtained by the steps of: preparing an O/W emulsion from an inner oil phase to become encapsulated oil droplets and a water phase containing a hydrophilic polymer gelling agent; dispersing and emulsifying the O/W emulsion into an outer oil phase so as to form an O/W/O emulsion; and hardening and capsulating the water phase of the O/W/O emulsion. FIG. 1 is a conceptual view of the microcapsule in accordance with the present invention. The microcapsule 2 has encapsulated oil droplets 1 (inner oil phase) therein.

The hydrophilic polymer gelling agent includes those usually used in cosmetics, medicines, and the like, which can harden to form a hydrophilic gel. Examples thereof include proteins such as gelatin or collagen, and polysaccharides such as agar, carrageenan, glucomannan, scleroglucan, schizophyllan, gellan gum, alginic acid, curdle, pectin, hyaluronic acid, or guar gum.

Among them, agar, carrageenan, and the like which harden by heating and cooling to form a gel are preferable in that they are less likely to be influenced by ions and in that the method of making the gel is simple, by which the gel can be hardened uniformly. In the present invention, it is preferred that such a hydrophilic polymer gelling agent hardening by heating and cooling is used as a main capsulating agent. Among them, agar and carrageenan are preferred from the viewpoints of properties, stability, feel of use, and the like of gel. In particular, agar is preferred. As agar, commercially available products such as Ina Agar PS-84, Z-10, AX-30, AX-100, AX-200, T-1, S-5, M-7 (manufactured by Ina Food Industry Co., Ltd.) can be used, for example.

In the present invention, two or more kinds of hydrophilic polymer gelling agents may be used together. Along with the hydrophilic polymer gelling agent hardening by heating and cooling, a hydrophilic polymer gelling agent, such as alginic acid, curdle, hyaluronic acid, or the like which hardens by ions such as Ca or by other coagulators can be used within a range which does not deteriorate the effect of the present invention.

Also, if necessary, other hydrophilic polymers, for example, such as synthetic polymers like polyacrylic acid, carboxymethyl cellulose, and cationized cellulose; and natural polymers such as xanthan gum and locust bean gum can be used within a range which does not deteriorate the effect of the present invention. In particular, the microcapsule tends to soften when Keltrol is used together with agar.

As the water phase, not only water but also ingredients and drugs which can be dissolved or dispersed in water can be contained.

The inner oil phase and outer oil phase of the present invention can be selected from a wide range of usually usable oils from polar oils to nonpolar oils, as long as they do not mix with the water phase and area liquid as a whole. Examples thereof include hydrocarbon oils, ester oils, higher alcohols, higher fatty acids, natural fats and oils, silicone oils, and the like. It is also possible to compound ingredients and drugs which can be dissolved or dispersed in these oils.

From the viewpoint of preventing the encapsulated oil droplet from infiltrating into the outer oil phase, it is preferred that the polarity of the inner oil phase differ from that of the outer oil phase.

In the preparation of the O/W emulsion preparing step, which is the first stage in the making of a microcapsule in accordance with the present invention, it is necessary to make a very fine and stable emulsion having an average particle size of 0.01 to 3 μm, preferably 0.01 to 1 μm. If the particle size is too large, then the fusion between inner oil phases and the unification between the inner and outer oil phases are likely to occur in the subsequent O/W/O emulsification step, whereby sufficient emulsification cannot be carried out. Also, loss in the inner oil phase tends to increase.

As a method of easily obtaining such an O/W emulsion, for example, an emulsifying method using a hydrophilic nonionic surfactant and a water-soluble solvent (Japanese Patent Publication No. 57-29213) can be applied effectively. Namely, an inner oil phase is added into a water-soluble solvent containing a hydrophilic nonionic surfactant so as to make an oil-in-water-soluble-solvent type emulsion, and an aqueous solution of a hydrophilic polymer gelling agent is added to this emulsion so as to prepare an O/W emulsion. The addition of hydrophilic polymer gelling agent may be carried out such that water is added to the oil-in-water-soluble-solvent type emulsion prepare an O/W emulsion, which is then diluted with the aqueous solution of a hydrophilic polymer gelling agent. Also, the hydrophilic polymer gelling agent can be added to the aqueous solvent beforehand as long as no problems occur in particular.

The water-soluble solvent dissolves the hydrophilic nonionic surfactant and efficiently makes the surfactant adsorb on the interface with respect to the oil phase which is subsequently added thereto. It can be selected from a very wide range of materials such as lower monohydric alcohols, lower polyhydric alcohols, ketones, aldehydes, ethers, amino, lower fatty acids, and others as long as they are hydrophilic and can dissolve the nonionic surfactant. Specific examples thereof include the water-soluble solvents disclosed in Japanese Examined Patent Publication No. 57-29213. In cosmetics and medicines, the water-soluble solvent is preferably a lower monohydric alcohol such as ethanol or propanol, or a lower polyhydric alcohol such as 1,3-butylene glycol or diethylene glycol. Here, the water-soluble solvent may contain therein a small amount of water, e.g., 15% by weight or less of water with respect to the water-soluble solvent.

As the hydrophilic nonionic surfactant, POE addition type or POE/POP addition type nonionic surfactant is preferable. Specific examples thereof include the hydrophilic nonionic surfactants disclosed in Japanese Examined Patent Publication No. 57-29213.

The preparation of O/W/O emulsion in the second stage is carried out by dispersing and emulsifying the O/W emulsion into the outer oil phase. The emulsifying apparatus used here is not restricted in particular, and it will be sufficient if a stirring apparatus usually used for emulsification is appropriately employed.

Preferably, a lipophilic surfactant is compounded as an emulsifier in the outer oil phase. As the lipophilic surfactant, any of ionic surfactants and nonionic surfactants can be used, and it will be sufficient if an appropriate one is selected from known lipophilic surfactants according to the kind of outer oil phase and the like.

When the water phase of such an O/W/O emulsion is hardened, a microcapsule containing a number of fine encapsulated oil droplets can be obtained.

A preferred method of making the microcapsule of the present invention comprises the steps of heating and dissolving a hydrophilic polymer gelling agent hardening by heating and cooling into water (which may contain other aqueous components as long as there are no problems) beforehand so as to prepare an aqueous gelling agent solution; adding it to the oil-in-water-soluble-solvent type emulsion at a hardening temperature of the gelling agent or higher so as to prepare an O/W emulsion; preparing an O/W/O emulsion therefrom while maintaining the temperature of the system at the hardening temperature or higher; and then cooling the system to the hardening temperature or lower so as to harden the water phase, thus making microcapsules. For example, in the case of agar and carrageenan, the hardening temperature is about 30° C., whereby it is preferred that the temperature for preparing the aqueous gelling agent is 90° C. to 100° C., whereas the temperature for preparing the emulsion is about 50° C. to 90° C.

In the case where the hydrophilic polymers hardening by addition of an ion and the like are used together, it will be favorable if a metal salt containing the ion or its aqueous solution is added to the O/W/O emulsion before cooling.

In the microcapsule of the present invention, since the inner oil phase is dispersed finely and stably at the O/W emulsion stage as mentioned above, the emulsifying condition upon preparing the O/W/O emulsion can be set freely, whereby the microcapsule diameter can be controlled easily. For example, the temperature and stirring speed at the time of O/W/O emulsification can take wide ranges of room temperature to about 90° C. and about 100 to 10,000 rpm, respectively. Even in such a case, there is no loss in the inner oil phase, and the encapsulated oil droplets hardly increase their diameter due to the inner oil phase fusion. The microcapsule diameter tends to decrease as the temperature and stirring speed at the time of O/W/O emulsification are higher, whereas it tends to increase as the concentration of the hydrophilic gelling agent and the viscosity of the outer oil phase are higher. According to the method of the present invention, the microcapsule diameter is controllable in a wide range of 5 to 1,000 $\mu$m.

The microcapsule of the present invention can change releasing characteristics of encapsulated oil droplets upon application according to its fracture strength. Here, since the fracture strength of the microcapsule itself cannot be measured directly, a gel prepared with the water phase composition is measured with a rheometer, and the result is taken as the fracture strength of the microcapsule.

If the fracture strength of the microcapsule is at least 10 g/cm$^2$ but less than 500 g/cm$^2$, preferably 30 to 400 g/cm$^2$, and its encapsulated oil droplets will be released rapidly when microcapsules applied on skin, and a favorable feel of use is obtained. If the fracture strength is too low, then its shearing-resistance will be insufficient. If the fracture strength is too high, then the capsule may be wholly or partly left undestroyed when applied as being spread over skin, whereby the encapsulated oil droplets may not be released rapidly. In the present invention, "shearing-resistance" means how hard to be destroyed the microcapsule is when added to the base materials for preparing products such as cream.

If the fracture strength of the capsule is at least 500 g/cm$^2$ but less than 2,000 g/cm$^2$, preferably 700 to 1,500 g/cm$^2$, a gradually-releasing characteristic of its encapsulated oil droplets and a favorable feel of use are obtained. If the fracture strength is too low, then its shearing-resistance will be insufficient, and substantially all the encapsulated oil droplets may be released upon application without exhibiting the gradually-releasing characteristic. If the fracture strength is too high, the microcapsule may not be released even after application.

As for the gradually-releasing characteristic of encapsulated oil droplets, it is presumed that, when a microcapsule is applied on skin, the microcapsule gel containing encapsulated oil droplets remains on the skin though the microcapsule is partly destroyed, and the encapsulated oil droplets are slowly released as moisture evaporates from the gel with time. As the microcapsule has a larger particle diameter, it can contain a greater amount of encapsulated oil droplets, whereby the gradually-releasing time tends to be longer.

If the fracture strength of the microcapsule is at least 2,000 g/cm$^2$ but 5,000 g/cm$^2$ or less, preferably 2,200 to 4,500 g/cm$^2$, its encapsulated oil droplets will be held within the microcapsule without being released even when applied on skin. If the fracture strength is too low, its shearing-resistance may be insufficient, and the encapsulated oil droplets may be released upon application. No enhancement of effects can be expected even if the fracture strength is made greater than the upper limit mentioned above.

Such a non-releasing microcapsule is particularly useful in sunscreen cosmetic products, makeup cosmetic products, and the like, for example. Inorganic pigments such as zinc oxide and titanium oxide are often compounded in these cosmetic products. However, if an organic UV-absorbing agent is used together with an inorganic pigment, a metal ion contained in the inorganic pigment and the organic UV-absorbing agent form a complex, whereby coloration may occur with time, thereby changing of color in product. Therefore, if such an organic UV-absorbing agent is compounded into a product as being encapsulated in a microcapsule, such that the organic UV-absorbing agent is held within the microcapsule even in the base material of the product or after application, it is possible to prevent change of color and direct contact between the UV-absorbing agent and skin.

The conventional microcapsules may be destroyed when added in emulsification steps and the like. Therefore, when compounding a microcapsule in an emulsification system, it has been necessary to prepare an emulsified product beforehand and then compound the microcapsule while stirring it slowly, whereby the steps have been complicated.

The microcapsule of the present invention has such a quite excellent shearing-resistance that the capsule is hardly destroyed even when added to an emulsifying step accompanying high-speed stirring. As a consequence, when the microcapsule is compounded in an emulsification system, emulsification can be effected after the microcapsule or its oily dispersion is compounded together with other ingredients. Also, it can be compounded in various other base materials.

Also, during the storage of the microcapsule of the present invention, encapsulated oil droplets hardly infiltrate into the microcapsule with time, whereby the inner oil phase does not substantially leak into the outer oil phase, and the microcapsule is substantially undestroyed. As a consequence, when an oil-soluble drug with a low stability is contained in encapsulated oil droplets, the stability of the drug can be improved. Examples thereof include easy-to-oxidize drugs such as retinol and vitamin E; and easy-to-crystallize drugs such as cyclosporin, vitamin C palmitate, and 4-tert-butyl-4'-methoxybenzoyl methane.

In particular, at the time of preparing an O/W emulsion, if a glyccryl higher fatty acid ester, a dextrin fatty acid ester, and the like are compounded as oily gelling agents in the oil phase, then the infiltration of encapsulated oil droplets can be suppressed remarkably. Here, the compounding amount of these oily gelling agents is 0.05% to 5% by weight, preferably 0.2% to 1% by weight in the inner oil phase. The infiltration preventing effect of the oily gelling agents may not fully be exhibited if the amount is too low, whereas they may affect other ingredients if the amount is too high.

In general, as for the elasticity of a gel, it is considered that one exhibiting a smaller Young's modulus is softer and more elastic, whereas one exhibiting a greater Young's modulus is harder and less elastic. Hence, the Young's modulus can be taken as an index for the feel of use when the microcapsule of the present invention is applied. In the present invention, the Young's modulus of the microcapsule is preferably set to 30 to 500 N/cm$^2$. In particular, if it is 30 to 300 N/cm$^2$, preferably 30 to 200 N/cm$^2$, then a smooth feel of use can be obtained. If the Young's modulus of the microcapsule is 300 to 500 N/cm$^2$, on the other hand, a massage effect (scrub effect) can be obtained. Here, as with the fracture strength of the microcapsule, a gel prepared with a water phase composition was measured with a rheometer, and the result is taken as the Young's modulus of the microcapsule.

A cosmetic preparation comprising the microcapsule not restricted in particular. Examples thereof include basic cosmetic preparation such as milky lotion, cream, lotion, cosmetic essence, cosmetic for massage, and scrub; washing preparations such as body soap and cleansing; makeup cosmetic products such as foundation, face powder, check rouge, lipstick, eye shadow, eye blow and mascara; and hair cosmetic products such as hair cream, hair tonic, hair treatment, hair growth promoting preparation, shampoo, and rinse. Its form may be emulsion, solution, liquid, solid, gel, mousse, spray, and the like. These are not restricted in particular as long as the effect of the present invention is not deteriorated thereby. Also, ingredients usually used in cosmetic products can be compounded in the cosmetic preparation of the present invention.

The microcapsule of the present invention can be compounded in other base materials in the state of an oily dispersion or after the outer oil phase 3 is partly or wholly eliminated by a normal method such as centrifuge or filtration. Also, it can be compounded in solid cosmetic preparations such as foundation and lipstick or in aqueous bases such as lotion. Preferably, the microcapsule of the present invention is stocked in an aqueous base or oily base material since it may contract when left in the air over a long period.

On the other hand, if a hydrophilic microcapsule such as the above-mentioned microcapsule is coated with a coating agent, then the contraction of the microcapsule can be suppressed when left in air. Also, the dispersibility of the microcapsule in a dispersion medium can be improved.

As the coating agent in the present invention, materials having a film-forming property and adsorptivity with respect to the hydrophilic microcapsule can be used.

Examples of lipophilic coating agent include solid hydrocarbons such as microcrystalline wax, vaseline, ceresinc or paraffin; waxes such as camauba wax, bees wax, or candelilla wax; higher fatty acids such as lauric acid, myristic acid, palmitic acid, stearic acid, or behenic acid; higher alcohols such as lauryl alcohol, cetanol, oleyl alcohol or stearyl alcohol; nitrocellulose; polyacrylate copolymer; highly polymerized methylpolysiloxane; and the like.

Examples of amphiphilic coating agent include allylated polysaccharides such as ethyl cellulose, propyl cellulose, hydroxyehyl cellulose, hydroxypropyl cellulose, ethylhydroxyethyl cellulose or alkylated xanthan gum; polyacrylic acid-polyacrylate copolymer; and the like.

Examples of hydrophilic coating agent include polymers such as polyvinyl alcohol, polyvinyl pyrrolidone or cationized cellulose; polysaccharides such as glucose or sucrose; and the like.

When these film-forming materials are employed as a coating agent, 0.1% to 200% by weight is added to the microcapsule for treating though depending on the coating method and the like. The effect may not be exhibited if the amount is too small, whereas the effect cannot be expected to enhance even if they are added in excess.

Surfactants such as hydrocarbon type surfactants, silicone type surfactants, and the like can also be used as a coating agent though their coating power is inferior to that of the above-mentioned film-forming materials. In this case, they are added by 5% to 100% by weight to the microcapsule for treating.

Examples of the hydrocarbon type surfactant include higher fatty acid salts such as magnesium stearate; ether type surfactants such as POE cetyl ether, POE oleyl ether or POE stearyl ether; ester type surfactants such as POE cetyl other stearate or POE stearyl ether stearate, amino acid derivatives such as N-acylglutamate; and the like. Examples of the silicone type surfactant include modified silicones such as POE methylpolysiloxane copolymer, POE/POP methylpolysiloxane copolymer or highly polymerized dimethysiloxane/methyl(aminopropyl)siloxane copolymer, and the like.

In the coated microcapsule of the present invention, the coating film suppresses the evaporation of water from the capsule, whereby the microcapsule itself hardly contracts even when loft in air. Though such a dry-resistance is exhibited in hydropililic coatings as well, lipophilic or amphiphilic coatings are preferable.

The microcapsule subjected to lipophilic or amphiphilic coating exhibits an improved dispersibility when dispersed in a lipophilic medium, whereas the microcapsule subjected to hydrophilic coating exhibits an improved dispersibility when dispersed in a hydrophilic medium.

Also, the coating film can suppress the elution of encapsulated components in the medium.

In the present invention, two or more kinds of coating agents may be mixed for treating, whereas different coating agents may be successively processed so as to laminate coating layers.

In the case where the capsulating agent of the hydrophilic microcapsule is agar, carrageenan, or the like, examples of particularly preferred coating agents include hydrophobic polysaccharides such as ethyl cellulose, propyl cellulose, hydroxyethyl cellulose, hydroxypropyl cellulose, ethylhydroxyethyl cellulose, and alkylated xanthan gum.

The coating for the hydrophilic microcapsule can be carried out, for example, by the steps of mixing the microcapsule and a coating agent in an appropriate solvent, eliminating the solvent, and then drying. As the solvent, although those in which the microcapsule is dispersible and the coating agent is soluble can be employed, a volatile solvent is preferable from the viewpoint of easiness in the eliminating operation. Examples thereof include volatile silicone oils; volatile hydrocarbon oils; lower alcohols such as ethanol and isopropanol; other volatile organic solvents; water; and the like, for example. Usually, a lipophilic solvent is used in the case of lipophilic or amphiphilic coating agents, whereas a hydrophilic solvent is used in the case of hydrophilic coating agents.

Also, coating can be effected if a solution in which a coating agent has been dissolved in a volatile solvent is sprayed over a microcapsule and then dried. Spraying and drying can be repeated a plurality of times. Known spraying apparatus can be selectively used as appropriate, and spraying may be effected while the microcapsule is stirred by use of appropriate stirring and mixing apparatus.

In any method, the drying method is not restricted in particular, whereby not only natural drying but also spray dry and granulating apparatus may be used. In order to accelerate drying, alcohol washing, heating, blowing, and the like may be effected as well.

As long as the effect of the present invention is not deteriorated, dissolution accelerating agent for accelerating the dissolution of coating agent may coexist in the medium. For example, polyhydric alcohol, alcohol, and the like can be used as a dissolution assistant in a hydrophilic solvent with respect to the hydrophilic coating agent.

An example of preferred coating method of the present invention comprises the steps of dispersing microcapsules into a volatile solvent; dissolving and mixing a coating agent therein; then evaporating the volatile solvent naturally or with blowing or heating if necessary; and drying. Also, microcapsules may be dispersed and mixed into a volatile solvent solution of a coating agent, and then the residue may be dried similarly. The method may comprise the steps of mixing microcapsules and a coating agent in a volatile solvent; then temporarily separating the microcapsule therefrom by filtration, centrifuge, or the like; and drying the residue thereafter. In this case, however, the coating amount of coating agent may decrease upon the separating operation, which requires the coating agent to be used at a relatively high concentration.

The hydrophilic microcapsule to be coated can be made by a known method. An example thereof comprises the steps of dispersing and emulsifying a water phase containing a hydrophilic polymer gelling agent into an oil phase so as to form a W/O emulsion; hardening and capsulating the water phase of the W/O emulsion; and eliminating the oil phase therefrom.

Also, as mentioned above, a microcapsule having an encapsulated oil droplet therein can be obtained by the steps of preparing an O/W emulsion from an inner oil phase and a water phase containing a hydrophilic gelling agent; dispersing and emulsifying the O/W emulsion in an outer oil phase so as to form an O/W/O emulsion; hardening and capsulating the water phase of the O/W/O emulsion; and then eliminating the outer oil phase. The microcapsule having encapsulated oil droplets is preferable in that it can encapsulate oil-soluble drugs within the microcapsule.

When such a hydrophilic microcapsule is coated with the lipophilic or amphiphilic coating agent, without separating the microcapsule from a microcapsule preparation liquid (oily dispersion), lipophilic or amphiphilic coating agents may be dissolved and mixed therein, the solvent may be eliminated, and the residue may be dried, so as to effect coating. In the case of hydrophilic coating, the microcapsule may be temporarily separated by filtration or the like, and processing may be carried out as mentioned above preferably after the microcapsule surface is washed with water or alcohol.

Depending on the kind of coating agent, the coated microcapsule of the present invention can exhibit a favorable dispersibility with respect to lipophilic to hydrophilic medium. Also, since it is very stable, it can be compounded in various base materials. Examples of coated microcapsule containing cosmetic preparations and their forms include those mentioned above, whereas ingredients usually used in cosmetic products can be compounded therein.

EXAMPLES

In the following, the present invention will be explained with reference to specific examples thereof. The compounding amount is indicated by wt % unless otherwise specified. Also, when a microcapsule oily dispersion without taking out the microcapsule is used, it will be mentioned as an oily dispersion.

I. Immediately-Releasing Microcapsule

Test Example I-1

(Microcapsule Ingredients)

| Inner oil phase: | |
|---|---|
| Perfume | 5 wt % |
| Dioctyl sebacate | 15 |
| Water phase: | |
| 1,3-Butylene glycol | 10 |
| POE(60) hardened caster oil | 1 |
| Agar | TABLE I |
| Ion-exchanged water | to 100 |

| -continued | |
|---|---|
| Outer oil phase: | |
| POE methylpolysiloxane copolymer | 1 |
| Octamethylcyclotetrasiloxane | 49 |

(Microcapsule Preparation Method)

The inner oil phase was gradually added to a mixture of 1,3-butylene glycol and POE (60) hydrogenated castor oil to obtain an oil-in-water-soluble-solvent type emulsion. Agar was dissolved in ion-exchanged water with heating at 90° C. to prepare an aqueous agar solution, which was then cooled to 50° C. The aqueous agar solution was added to the oil-in-water-soluble-solvent type emulsion heated to 50° C. while being stirred, whereby an O/W emulsion (average particle size: 0.5 $\mu$m) was obtained.

The O/W emulsion was added to the outer oil phase, and the mixture was emulsified at 50° C.×500 rpm to prepare an O/W/O emulsion. It was gradually cooled to room temperature to harden agar in the water phase, thereby obtaining a maicrocapsule oily dispersion (average microcapsule particle size: 100 $\mu$m; average encapsulated oil droplet particle size: 0.5 $\mu$m).

In the present invention, the average particle size of encapsulated oil droplets was measured by a dynamic light scattering method (using a dynamic light scattering photometer DLS-700 manufactured by Otsuka Electronics Co., Ltd.), whereas the average particle size of microcapsule was determined from the particle size distribution measured by a laser diffraction/scattering type particle size distribution measuring apparatus (manufactured by Horiba, Ltd.).

(Fracture Strength and Young's modulus of Microcapsule)

The water phase was heated and dissolved at 90° C. and then cooled to prepare a gel with a thickness of 32 mm. The fracture strength and Young's modulus of this gel were measured by a rheometer (RM-2010-CW manufactured by Fudo Kogyo Co., Ltd.), and were taken as the fracture strength and Young's modulus of the capsule.

The measuring conditions were as follows:

range: 200 g test speed: 5 cm/min sweep speed: 5 cm/min adapter diameter: 10 mm at a fracture strength of less than 500 g/cm$^2$ 3 mm at a fracture strength of 500 g/cm$^2$ or greater detector: 2 kg (Shearing-Resistance)

The stability of the microcapsule when added to an emulsifying step (shearing-resistance) was studied as follows. Namely, a W/O cream containing the microcapsule was prepared with the following ingredients. The W/O emulsification was carried out by a homomixer at 70° C.×9,000 rpm.

Whether the microcapsule in the obtained cream was destroyed or not was observed through a microscope, and the case where destruction of the microcapsule was seen was indicated with "X" for shearing-resistance, whereas the case where no destruction was seen was indicated with "○" for shearing-resistance.

Cream Ingredients for Shearing-Resistance Test:

| | |
|---|---|
| Microcrystalline wax | 9.0 wt % |
| Solid paraffin | 2.0 |
| Bees wax | 3.0 |
| Vaseline | 5.0 |
| Squalane | 34.0 |
| Hexadecyl adipate | 10.0 |
| Propylene glycol | 5.0 |
| Glyceryl monooleate | 3.5 |
| POE(20) sorbitan monooleate | 1.0 |
| Purified water | 22.5 |
| Microcapsule oily dispersion | 5.0 |
| Antiseptic | Q.S. |
| Perfume | Q.S. |

(Releasing Test)

The microcapsule oily dispersion and an ethanol solution containing 5% fragrance (control) were put on the inside of left and right wrists by 0.1 g each with a spatula, respectively. The strength of scent (fragrance scent) with reference to the control was evaluated before being spread (shown as "before") and immediately after being spread (shown as "after") with a finger tip according to the following standard:

Evaluation Standard

⊚: as strong as the control

○: slightly weaker than the control

Δ: weaker than the control

X: substantially no scent

TABLE 1

| Sample | | Agar | Fracture | Shearing- | Releasing test | |
|---|---|---|---|---|---|---|
| No. | Name | Amount | strength | resistance | Before | After |
| 1 | T-1 | 0.1% | 5 g/cm² | X | X | ⊚ |
| 2 | AX-30 | 1.0 | 30 | ○ | X | ⊚ |
| 3 | PS-84 | 0.7 | 200 | ○ | X | ⊚ |
| 4 | AX-200 | 1.5 | 400 | ○ | X | ⊚ |
| 5 | PS-84 | 1.5 | 1,323 | ○ | X | Δ |

The shearing-resistance was insufficient in Sample 1. In Sample 5, while the shearing-resistance was favorable, the scent was weaker than that of the control immediately after the sample was spread on the skin as being rubbed. It is assumed to be because of the fact that encapsulated oil droplets are not rapidly released from the microcapsule upon rubbing at the time of application.

In Samples 2 to 4, by contrast, while the scent was hardly felt when simply put on skin, the scent as strong as that of the control was felt when spread on the skin as being rubbed, from which it was assumed that encapsulated oil droplets were substantially released from the microcapsule upon rubbing at the time of application.

Therefore, for exhibiting a shearing-resistance and a immediately-releasing characteristic of encapsulated oil droplets, it is preferred that the fracture strength of the microcapsule is at least 10 g/cm² but less than 500 g/cm², and is 30 to 400 g/cm² in particular.

Test Example I-2

Microcapsules prepared by use of a two-stage emulsifying method (Examples I-1, I-2) and those prepared by a conventional method (Comparative Examples I-1, I-2) were compared with each other. In each case, the average particle size of O/W emulsion was set to 0.5 μm. The fracture strength of each gel prepared with a water phase was 400 g/cm². Results are shown in TABLE 2.

TABLE 2

| | Ex. I-1 | Ex. I-2 | Comp.Ex. I-1 | Comp.Ex I-2 |
|---|---|---|---|---|
| O/W/O emulsifying condition | | | | |
| Temperature(° C.) | 50 | 70 | 50 | 70 |
| Stirring rate(rpm) | 500 | 2,500 | 500 | 2,500 |
| Average particle size(μm) | | | | |
| Encapsulated oil droplet | 0.5 | 0.5 | 10 | not obtained |
| Microcapsule | 100 | 50 | 500 | not obtained |
| Inner oil phase capsulating rate(%) | 100 | 100 | 70 | — |
| Shearing-resistance | ○ | ○ | X | — |

While the encapsulated oil droplet diameter in Examples was substantially the same as the emulsified particle size at the time of preparing the O/W emulsion, the encapsulated oil droplet diameter in Comparative Examples increased up to 10 μm. It is assumed to be because of the fact that the O/W emulsion was unstable in Comparative Examples, whereby the inner oil phase fusion remarkably occurred at the time of O/W/O emulsification.

Also, the capsulating rate was nearly 100% in each of the respective cases where the O/W/O emulsifying condition was 50° C.×500 rpm (mild emulsifying condition) and 70° C.×2,500 rpm (severe emulsifying condition), whereby no loss in the inner oil phase occurred in any case. In Comparative Examples, by contrast, even an under the emulsifying condition of 50° C.×500 rpm, capsulating rate was low, and loss in the inner oil phase was remarkable. Further, no O/W/O emulsion was obtained under a severer condition with stirring at a higher temperature or higher speed. It suggested that not only the fusion between inner oil phases but also the unification between inner and outer phases occurred in Comparative Examples.

Also, while the microcapsules of Examples were excellent in shearing-resistance since they were not destroyed when added in the emulsifying step, destruction often occurred in the microcapsules of Comparative Examples.

Further, after being stored for 2 months at 50° C., the microcapsule oily dispersions of Examples maintained substantially 100% of the inner oil phase capsulating rate.

As in the foregoing, the emulsifying condition in the making of the microcapsule of the present invention can be set freely, whereby the particle size of microcapsule can be controlled easily. Also, it can be understood that the inner oil phase has a high capsulating rate, and yields no loss at the time of making.

The ingredients and preparation method of microcapsules of TABLE 2, and the measurement method of the inner oil phase capsulating rate are as follows.

(Example Microcapsule)

| | |
|---|---|
| Inner oil phase: | |
| (1)Vitamin A palmitate | 5 wt % |
| (2)Cetyl isooctanoate | 5 |
| Water phase: | |
| (3)POE(60) hardened caster oil | 0.5 |
| (4)Glycerin | 10 |

-continued

| | |
|---|---|
| (5)Agar(PS-84) | 1 |
| (6)Ion-exchanged water | 28.5 |
| Outer oil phase: | |
| (7)POE methylpolysiloxane copolymer | 0.5 |
| (8)Dimethylpolysiloxane(6 cps) | 49.5 |
| Total | 100.0 |

Preparation method:

(1) and (2) were mixed to prepare an inner oil phase. The inner oil phase was gradually added to a mixture of (3), (4) and 0.5% of (6) to obtain an oil-in-water-soluble-solvent type emulsion. (5) was dissolved in 28% of (6) with heating at 90° C. to prepare an aqueous solution of agar. The agar aqueous solution cooled to 50° C. was added to the oil-in-water-soluble-solvent type emulsion heated at 50° C. while being stirred to obtain an O/W emulsion.

The O/W emulsion was added and emulsified in a mixture of (7) and (8) while maintaining predetermined temperature to prepare an O/W/O emulsion. The O/W/O emulsion was gradually cooled to the room temperature to harden agar of the water phase, thereby obtaining a microcapsule oily dispersion.

(Comparative Example Microcapsule)

| | |
|---|---|
| Inner oil phase: | |
| (1)Stearic acid | 2 wt % |
| (2)Squalane | 10 |
| Water phase: | |
| (3)Sorbitan monooleate | 2 |
| (4)Glycerin | 5 |
| (5)Agar(PS-84) | 1 |
| (6)Ion-exchanged water | 30 |
| Outer oil phase: | |
| (7)POE methylpolysiloxane copolymer | 0.5 |
| (8)Dimethylpolysiloxane(6 cps) | 49.5 |
| Total | 100.0 |

Preparation method:

(1) and (2) were mixed to prepare an inner oil phase. The inner oil phase was added and emulsified in a mixture of (3), (4) and 13% of (6) to obtain an to obtain an O/W emulsion. (5) was dissolved in the rest of (6) with heating at 90° C. to prepare an aqueous solution of agar. The agar aqueous solution cooled to 50° C. was added to the O/W emulsion heated at 50° C.

After this, in the same way as the preparation method of the Example microcapsule mentioned above, preparation was carried out.

(Inner Oil Phase Capsulating Rate)

Microcapsule oily dispersion prepared by adding 0.2 wt % of ethyl γ-linolenate to the inner oil phase was centrifuged, and the amount of ethyl γ-linolenate in the outer oil phase was determined by high-performance liquid chromatography. The capsulating rate was calculated from the amount of ethyl γ-linolenate added in the inner oil phase and that determined in the outer oil phase by the following expression:

Capsulating rate(%)={(amount added−amount in the outer oil phase)/amount added}×100

Test Example I-3

| | |
|---|---|
| Inner oil phase: | |
| (1)Vitamin A palmitate | 5 wt % |
| (2)Squalane | 9.5 |
| Water phase: | |
| (3)POE(60) hardened caster oil | 0.5 |
| (4)1,3-Butylenegrycol | 10 |
| (5)Carrageenan | 1 |
| (6)Ion-exchanged water | 24 |
| Outer oil phase: | |
| (7)POE methylpolysiloxane copolymer | 1 |
| (8)Dimethylpolysiloxane(6 cs) | 48 |
| (9)Benton 38 | 1 |
| Total | 100.0 |

(Preparation Method)

(1) and (2) were mixed to prepare an inner oil phase. The inner oil phase was gradually added to a mixture of (3), (4) and 0.5% of (6) to obtain an oil-in-water-soluble-solvent type emulsion. (5) was dissolved in the rest of (6) with heating at 90° C. to prepare an aqueous solution of carrageenan. The carrageenan aqueous solution cooled to 50° C. was added to the oil-in-water-soluble-solvent type emulsion heated at 50° C. while being stirred to obtain an O/W emulsion(average particle size: 0.5 μm).

The O/W emulsion was added to a mixture of (7), (8) and (9), and emulsified under a condition of 50° C.×7,000 rpm to prepare an O/W/O emulsion. The O/W/O emulsion was gradually cooled to the room temperature to harden carrageenan of the water phase, thereby obtaining a microcapsule oily dispersion.

The average particle size of the microcapsule and the encapsulated oil droplet were 10 μm and 0.5 μm, respectively. Also, the inner oil phase capsulating rate was 100%. Further, the fracture strength of the microcapsule was 200 g/cm².

Compounding Example I-1 O/W Cream (Microcapsule Ingredients)

TABLE 3

| Ingredients | Microcapsule 1 | Microcapsule 2 |
|---|---|---|
| Inner oil phase: | | |
| Cyclosporin | 5 | — |
| Crotamiton | 15 | — |
| Vitamin C dipalmitate | — | 2.5 |
| Dioctyl sebacate | — | 15 |
| Water phase: | | |
| 1,3-Butylene glycol | 10 | 10 |
| POE(60) hardened caster oil | 1 | 1 |
| Agar(AX-200) | 1.5 | 1.5 |
| Ion-exchanged water | 17.5 | 20 |
| Outer oil phase: | | |
| POE methylpolysiloxane copolymer | 1 | 1 |
| Octamethylcyclotetrasiloxane | 49 | 49 |

(Microcapsule Preparation Method)

According to Example of Test Example I-2, by using the ingredients of TABLE 3, an microcapsule oily dispersion was prepared and filtrated to obtain a microcapsule. The fracture strength of each microcapsule was 400 g/cm².

(Cream Preparation)

With the ingredients of TABLE 4, O/W creams were prepared by a normal method. They were stored at 0° C., room temperature, and 50° C., and whether crystals deposited or not were observed by the naked eye with time until 1 month thereafter. Results are shown in TABLE 4.

TABLE 4

| Ingredients | Cream A | B | C | D |
|---|---|---|---|---|
| Stearyl alcohol | 6 | 6 | 6 | 6 |
| Stearic acid | 2 | 2 | 2 | 2 |
| Hydrogenated lanolin | 4 | 4 | 4 | 4 |
| Squalane | 9 | 9 | 3 | 3 |
| Octyldodecanol | 10 | 10 | 10 | 10 |
| Cyclosporin | — | — | 2 | — |
| Crotamiton | — | — | 6 | — |
| Vitamin C dipalmitate | — | — | — | 1 |
| Dioctyl sebacate | — | — | — | 6 |
| 1,3-Butylene glycol | 6 | 6 | 6 | 6 |
| PEG 1500 | 4 | 4 | 4 | 4 |
| POE(25) cetyl alcohol | 3 | 3 | 3 | 3 |
| Glyceryl monostearate | 2 | 2 | 2 | 2 |
| Purified water | 34 | 34 | 52 | 53 |
| Microcapsule 1 | 20 | — | — | — |
| Microcapsule 2 | — | 20 | — | — |
| Antiseptic | Q.S. | Q.S. | Q.S. | Q.S. |
| Antioxidant | Q.S. | Q S. | Q.S. | Q.S. |
| Crystal deposit (0° C. × 3 days) | none | none | exist | exist |
| (0° C. × 1 month) | none | none | exist | exist |
| (r.t. × 2 weeks) | none | none | exist | exist |
| (r.t. × 1 month) | none | none | exist | exist |
| (50° C. × 2 weeks) | none | none | none | none |
| (50° C. × 1 month) | none | none | exist | exist |

Drugs such as cyclosporin and vitamin C dipalmitate are hard to dissolve in solvents and easy to crystallize, so that, though they can be temporarily dissolved in a solvent upon heating to be compounded, crystal deposition may be seen with time (Creams C and D).

In the case where a microcapsule encapsulating these drugs was compounded, by contrast, as with Creams A and B, no crystal deposition was seen at all.

Therefore, the microcapsule of the present invention is very stable, whereby using it can realize a product which can stably contain drugs that have conventionally been hard to be compound and rapidly releases these drugs when applied on skin.

Also, a large amount of water-soluble drugs can be stably encapsulated in the water phase, whereby the microcapsule of the present invention is useful for preparations in which water-soluble drugs have conventionally been hard to be compound.

Compounding Example I-2 Lipstick (Microcapsule Ingredients)

| Inner oil phase: | |
|---|---|
| Retinol | 5 wt % |
| Dioctyl sebacate | 15 |
| Water phase: | |
| 1,3-Butylene glycol | 10 |
| POE(60) hardened caster oil | 1 |
| Agar(S-5) | 1.5 |
| Ascorbic acid 2-glucoside | 5 |
| Ion-exchanged water | 12.5 |

| Outer oil phase: | |
|---|---|
| POE methylpolysiloxane copolymer | 1 |
| Octamethylcyclotetrasiloxane | 49 |

(Microcapsule Preparation Method)

With the above ingredients, according to Test Example I-2, a microcapsule oily dispersion was prepared and then filtrated to obtain microcapsules (fracture strength of the microcapsule: 350 g/cm$^2$).

(Lipstick Preparation)

| Titanium dioxide | 5 wt % |
|---|---|
| Red #201 | 0.6 |
| Red #202 | 1 |
| Red #223 | 0.2 |
| Candelilla wax | 9 |
| Solid paraffin | 8 |
| Bees wax | 5 |
| Carnauba wax | 5 |
| lanolin | 11 |
| Caster oil | 5.2 |
| Cetyl 2-ethythexanoate | 20 |
| Isopropyl myristate | 10 |
| Microcapsule | 20 |
| Antioxidant | Q.S. |
| Perfume | Q.S. |

A solid lipstick was prepared by a normal method. In normal lipsticks, easy-to-oxidize drugs such as retinol have been hard to be compounded due to their formulations, and water-soluble humectants such as ascorbic acid derivatives and the like cannot be compounded due to their formulations. If the microcapsule of the present invention is used, such drugs can be stably compounded in lipsticks, whereby those having wrinkle-improvement and moisturizing effects can be obtained.

Compounding Example I-3 Check Rouge

| Kaoline | 20 wt % |
|---|---|
| Titanium dioxide | 4.2 |
| Iron oxide (red) | 0.3 |
| Red #202 | 0.5 |
| Ceresine | 15 |
| Liquid paraffin | 15 |
| Isopropyl myristate | 5 |
| Microcapsule(Compounding Example I-2) | 20 |
| Antioxidant | Q.S. |
| Perfume | Q.S. |

Compounding Example I-4 O/W Foundation

O/W foundations were prepared by a normal method, and whether there was a change of color or not after being stored for 1 month at 50° C. was observed with the naked eye. Results are shown in TABLE 5.

A change of color was seen in Foundation B in which vitamin E acetate was compounded as it was. It is assumed to be because of the fact that vitamin E was decomposed due to metal ions contained in inorganic pigments.

By contrast, no change of color was seen in Foundation A in which a microcapsule encapsulating vitamin E acetate was compounded.

TABLE 5

| Ingredients | Foundation A | Foundation B |
|---|---|---|
| Talc | 3 | 3 |
| Titanium dioxide | 5 | 5 |
| Bentonite | 0.5 | 0.5 |
| Microcapsule* | 10 | — |
| POE sorbitan monostearate | 0.9 | 0.9 |
| Triethanolamine | 1 | 1 |
| Propylene glycol | 10 | 10 |
| Vitamin E acetate | — | 1 |
| Ion-exchanged water | 48.4 | 57.4 |
| Stearic acid | 2.2 | 2.2 |
| Isohexadecyl alcohol | 7 | 7 |
| Glyceryl monostearate | 2 | 2 |
| Liquid lanolin | 2 | 2 |
| Liquid paraffin | 8 | 8 |
| Antiseptic | Q.S. | Q.S. |
| Antioxidant | Q.S. | Q.S. |
| Perfume | Q.S. | Q.S. |
| Change of color(50° C., 1 month) | none | exist |

*It was prepared according to the microcapsule of Compounding Example I-2 with vitamin E acetate in the place of retinol.

Compounding Example I-5 Jelly-like peel-off pack

| | |
|---|---|
| Polyvinyl alcohol | 15 wt % |
| Carboxymethyl cellulose | 5 |
| 1,3-Butylene glycol | 5 |
| Ethanol | 5 |
| POE oleyl alcohol | 0.5 |
| Microcapsule(Compounding Example I-2) | 10 |
| Ion-exchanged water | 59.5 |

Jelly-like peel-off pack was prepared by a normal method. Since normal jelly-like packs are aqueous, oils and oil-soluble drugs are bard to be compounded therein. By contrast, using the microcapsule of the present invention can yield a pack which can stably contain oils and oil-soluble drugs therein, and rapidly release these encapsulated materials therefrom upon application.

Compounding Example I-6 Capsule-containing Sheet

| | |
|---|---|
| (1)1,3-Butylene glycol | 15 wt % |
| (2)Polyvinyl alcohol | 5 |
| (3)Microcapsule(Compounding Example I-2) | 50 |
| (4)Ethanol | 10 |
| (5)PEG 6000 | 3 |
| (6)PEG 1200 | 2 |
| (7)POE(25) hardened castor oil | 5 |
| (8)Stearic acid | 10 |

(Preparation Method)

(1), (2), (5) and (6) were dissolved with stirring and a mixed solution of (4), (7) and (8) was added thereto. Further, (3) was added to the mixture and then stirred to obtain microcapsule-containing liquid. This liquid was soaked into a sheet such as nonwoven fabric and the like to obtain a sheet type product.

Compounding Example I-7 Deodorant Powder Spray (Microcapsule Ingredients)

| | |
|---|---|
| Inner oil phase: | |
| (1) Zinc paraphenolsulfonate | 4.25 wt % |
| (2) Squalane | 4 |
| (3) Triclosan | 0.25 |
| (4) Isopropyl myristate | 2.5 |
| Water phase: | |
| (5) 1,3-Butylene glycol | 10 |
| (6) POE(60) hardened castor oil | 1 |
| (7) Agar(AX-100) | 1 |
| (8) Gellan gum | 0.3 |
| (9) Citric acid | 0.1 |
| (19)Sodium citrate | 0.1 |
| (11)Ascorbic acid 2-glucoside | 2.5 |
| (12)Ion-exchanged water | 24.0 |
| (13)Antioxidant | Q.S. |
| Outer oil phase: | |
| (14)POE methylpolysiloxane copolymer | 1 |
| (15)Octadecylcyclotetrasiloxane | 49 |

(Microcapsule Preparation Method)

The inner oil phase was gradually added to a mixture of (5), (6) and 0.5% of (12) to obtain an oil-in-water-soluble-solvent type emulsion. (7), (8), (11) and (13) were dissolved in 10% of (12) with heating at 90° C. to prepare a gelling agent aqueous solution. The gelling agent aqueous solution cooled to 50° C. was added to the oil-in-water-soluble-solvent type emulsion heated at 50° C. while being stirred to obtain an O/W emulsion.

The O/W emulsion was added to the outer oil phase and emulsified at 50° C. to prepared an O/W/O emulsion. The emulsion, with a mixed aqueous solution of (9), (10) and the rest of (12) added thereto, was stirred sufficiently and gradually cooled to the room temperature to prepare a microcapsule oily dispersion. The dispersion was filtrated to obtain microcapsules (fracture strength of the microcapsule: 100 g/cm$^2$).

(Stock Solution for Spray)

| | |
|---|---|
| Aluminum chlrohydrate | 30 wt % |
| Silicic anhydride | 15 |
| Siliconizing talc | 15 |
| Zinc oxide | 5 |
| Microcapsule | 20 |
| Dimethylpolysiloxane | 12 |
| Sorbitan stearate | 3 |

(Spray Preparation Method)

10 weight parts of the stock solution and 90 weight parts of LPG were filled into a spray can.

Compounding Example I-8 Semitransparent Lotion

| | |
|---|---|
| (1)1,3-Butylene glycol | 6 wt % |
| (2)Glycerin | 5 |
| (3)Polyethylene glycol 400 | 3 |
| (4)Olive oil | 0.5 |
| (5)POE(20) sorbitan monostearate | 1.5 |
| (6)Ethanol | 5 |
| (7)Microcapsule(ExampleI-1) | 5.3 |
| (8)Purified water | 73.7 |

-continued

| (9)Perfume | Q.S. |
|---|---|
| (10)Antiseptic | Q.S. |

(Preparation Method)

(1) was added to (8)(water phase). (2) to (5), (9) and (10) were added to (6) and mixed at the room temperature (alcohol phase). The alcohol phase was added to the water phase and stirred within (7) added thereto, thereby obtaining a lotion.

Compounding Example I-9 O/W Emollient Lotion

| (1)Stearic acid | 2 wt % |
|---|---|
| (2)Cetyl alcohol | 1.5 |
| (3)Vaseline | 4 |
| (4)Squalane | 5 |
| (5)Glyceryl tri-2-ethylhexanoate | 2 |
| (6)Sorbitan monooleate | 2 |
| (7)Dipropylene glycol | 5 |
| (8)Polyethylene glycol 1500 | 3 |
| (9)Triethanolamine | 1 |
| (10)Microcapsule(ExampleI-2, oily dispersion) | 10 |
| (11)Purified water | 64.5 |
| (12)Perfume | Q.S. |
| (13)Antiseptic | Q.S. |

(Preparation Method)

(7), (8) and (9) were added to (11) and heated to 70° C. (water phase). (6), (12) and (13) were added to a mixed solution of (1) to (5) and heated to 70° C. (oil phase). The oil phase was added to the water phase and the mixture was emulsified by a homomixer and then stirred with (10) added thereto. The emulsion was deaerated, filtrated and cooled to obtain an emollient lotion.

Compounding Example I-10 W/O Massage Cream

| (1)Microcrystalline wax | 9 wt % |
|---|---|
| (2)Solid paraffin | 2 |
| (3)Bees wax | 3 |
| (4)Vaseline | 5 |
| (5)Hydrogenated lanolin | 5 |
| (6)Squalane | 30 |
| (7)Hexadecyl adipate | 1 |
| (8)Propylene glycol | 5 |
| (9)Glyceryl monooleate | 3.5 |
| (10)POE(20) sorbitan monooleate | 1 |
| (11)Microcapsule(ExampleI-2, oily dispersion) | 4 |
| (12)Purified water | 30.5 |
| (13)Perfume | Q.S. |
| (14)Antiseptic | Q.S. |

(Preparation Method)

(9), (10), (13) and (14) were added to a mixture of (1) to (7) dissolved with heating, and then heated to 70° C. (oil phase). (8) was added to (12) and then heated to 70° C. (water phase). The oil phase and the water phase were mixed and emulsified by a homomixer and further mixed with (11) added thereto. The emulsion was deaerated, filtrated, and cooled to obtain a cream.

Compounding Example I-11 W/O Emollient Cream

| (1)Squalane | 20 wt % |
|---|---|
| (2)Cetyl isooctanoate | 8.5 |
| (3)Microcrystalline wax | 1 |
| (4)Organophilic clay mineral | 1.3 |
| (5)POE glyceryl triisostearate | 0.2 |
| (6)Glycerin | 5 |
| (7)Microcapsule(ExampleI-1, oily dispersion) | 5 |
| (8)Purified water | 59 |
| (9)Perfume | Q.S. |
| (10)Antiseptic | Q.S. |

(Preparation Method)

(4), (5), (9) and (10) were added to a mixture of (1) to (3) dissolved with heating. After being heated to 70° C., the mixture was suspended and dissolved uniformly to obtain an oily gel. (6) was added to (8) and heated to 70° C. (water phase). The water phase was gradually added to the oily gel while being stirred sufficiently, and mixed by a homomixer uniformly. The mixture was further mixed with (7) added thereto, deaerated, filtrated, and then cooled to obtain a cream.

Compounding Example I-12 Moisture Gel

| (1)Dipropylene glycol | 7 wt % |
|---|---|
| (2)Polyethylene glycol 1500 | 8 |
| (3)Carboxyvinyl polymer | 0.4 |
| (4)Methyl cellulose | 0.2 |
| (5)POE(15) oleyl ether | 1 |
| (6)Potassium hydroxide | 0.1 |
| (7)Microcapsule(ExampleI-1) | 1 |
| (8)Purified water | 82.3 |
| (9)Perfume | Q.S. |

(Preparation Method)

(6) was dissolved in a part of (8) to prepare a basic aqueous solution. (3) and (4) were dissolved in the rest of (8) uniformly and (2) was added thereto (water phase). (5) was added and dissolved into (1) with heating at 50° C., and (9) was added thereto. The water phase was gradually added to the mixture while being stirred and stirred with the basic aqueous solution added thereto. (7) was added to the mixture and sufficiently stirred to obtain a gel.

Compounding Example I-13 O/W Emollient Cream (Microcapsule Ingredients)

| Inner oil phase: | |
|---|---|
| (1)Squalane | 10 wt % |
| (2)Lecithin | 1 |
| Water phase: | |
| (3)POE(60) hardened caster oil | 0.5 |
| (4)Glycerin | 10 |
| (5)Thyme extract | 1 |
| (6)Agar(PS-84) | 1 |
| (7)Ion-exchanged water | 26.5 |
| Oil phase: | |
| (8)POE methylpolysiloxane copolymer | 0.5 |
| (9)Dimethylpolysiloxane(6 cps) | 49.5 |

(Microcapsule Preparation Method)

(2) was dissolved in (1) with heating at 50° C. to prepare an inner oil phase. The inner oil phase was gradually added to a mixture of (3), (4), (5) and 0.5% of (7) to obtain an oil-in-water-soluble-solvent type emulsion. (6) was dissolved in 26% of (7) with heating at 90° C. to prepare an agar aqueous solution. The agar aqueous solution cooled at 50° C. was added to the oil-in-water-soluble-solvent type emulsion heated at 50° C. while being stirred to obtain an O/W emulsion (average particle size: 0.5 μm).

The O/W emulsion was added to a mixture of (8) and (9) while being maintained at 50° C. and emulsified to prepare an O/W/O emulsion. The O/W/O emulsion was gradually cooled to the room temperature to harden the agar of the water phase, thereby obtaining a microcapsule oily dispersion.

(Emollient Cream Ingredients)

| | |
|---|---|
| (1)Squalane | 5 wt % |
| (2)Acrylic acid/alkyl methacrylate copolymer | 0.1 |
| (3)Carboxyvinyl polymer | 1.0 |
| (4)Sodium hydroxide | 0.2 |
| (5)Glycerin | 15 |
| (6)Microcapsule | 8 |
| (7)Purified water | 69.7 |
| (8)Perfume | Q.S. |
| (9)Antiseptic | Q.S. |

(Emollient Cream Preparation Method)

(2) to (5) and (9) were added to (6) to prepare a water phase. (8) was added to (1) to prepare an oil phase. The oil phase was added to the water phase and the mixture was mixed and emulsified by a homomixer. The emulsion was further mixed with (6) added thereto, deaerated and filtrated to obtain an O/W emollient cream.

Compounding Example I-14 W/O Emollient Cream

| | |
|---|---|
| (1)Squalane | 5 wt % |
| (2)Vaseline | 5 |
| (3)POE glyceryl isostearate | 3 |
| (4)Glyceryl isostearate | 3 |
| (5)Glycerin | 10 |
| (6)Microcapsule(Compounding Example I-13, oily dispersion) | 10 |
| (7)Purified water | 63 |
| (8)Perfume | Q.S. |
| (9)Antiseptic | Q.S. |

(Preparation Method)

(5) and (9) were added to (7) and heated to 70° C. (water phase). (2) to (4) and (8) were added to (1) and the mixture was dissolved with heating to 70° C. (oil phase). The oil phase and the water phase were mixed and emulsified by a homomixer, and then further mixed with (6) added thereto. The mixture was deaerated, filtrated, and cooled to obtain a W/O emollient cream.

II. Gradually-Releasing Microcapsule

Test Example II-1

Microcapsules were prepared in the same way as Test Example I-1 mentioned above except for using agar in TABLE 6 as a gelling agent. The shearing-resistance and fracture strength of the Microcapsules were studied. Also, its gradually-releasing characteristic was examined according to the following method.

(Gradually-Releasing Test)

The microcapsule oily dispersion and an ethanol solution containing 5% fragrance (control) were put on the inside of left and right wrists by 0.1 g each with a spatula, respectively. The strength of scent (fragrance scent) was evaluated before being spread (shown as "before"), immediately after being spread with a finger tip (shown as "after"), 1, 3, 6, and 12 hours thereafter according to the following standard:

Evaluation Standard

⊚: strong scent

○: relatively strong scent

Δ: weak scent

X: substantially no scent

TABLE 6

| | Agar | | Fracture | Shearing- | Gradually-releasing test | | | | | |
|---|---|---|---|---|---|---|---|---|---|---|
| No. | Name | Amount | strength | resistance | Before | After | 1 hr | 3 hr | 6 hr | 12 hr |
| 1 | T-1 | 0.1% | 5 g/cm² | x | x | ⊚ | ○ | Δ | x | x |
| 2 | AX-200 | 1.5 | 400 | ○ | x | ⊚ | ○ | Δ | x | x |
| 3 | M-7 | 0.5 | 700 | ○ | x | ○ | ○ | ○ | ○ | Δ |
| 4 | PS-84 | 1.5 | 1,323 | ○ | x | ○ | ○ | ○ | ○ | Δ |
| 5 | S-5 | 3.0 | 1,500 | ○ | x | ○ | ○ | ○ | ○ | Δ |
| 6 | PS-84 | 3.0 | 2,274 | ○ | x | x | x | x | x | x |
| Control | | | — | — | ⊚ | ⊚ | ○ | Δ | x | x |

The shearing-resistance was insufficient in Sample 1. In Sample 2, while the shearing-resistance was favorable, the scent was not different from that of the control in the releasing characteristic. Therefore, it can be considered that almost of perfume was released from the microcapsule at the time of application. Also, because the scent was hardly felt in Sample 6, whereby it was assumed that the perfume in the microcapsules was not released.

In Samples 3 to 5, by contrast, the remaining time of the scent was very long, whereby the perfume was released from the microcapsule gradually.

Therefore, for exhibiting a shearing-resistance and a gradually-releasing characteristic of encapsulated oil droplets, it is preferred that the fracture strength of the microcapsule is at least 500 g/cm² but less than 2,000 g/cm², and is 700 to 1,500 g/cm² in particular.

Test Example II-2

Microcapsules prepared by use of a two-stage emulsifying method (Examples II-1, II-2) and those prepared by a conventional method (Comparative Examples II-1, II-2) were compared with each other. In each case, the average particle size of O/W emulsion was set to 0.5 μm. The fracture strength of each gel prepared with a water phase was 1,000 g/cm². Results are shown in TABLE 7.

TABLE 7

|  | Ex. II-1 | Ex. II-2 | Comp.Ex. II-1 | Comp.Ex II-2 |
|---|---|---|---|---|
| O/W/O emulsifying condition | | | | |
| Temperature(° C.) | 50 | 70 | 50 | 70 |
| Stirring rate(rpm) | 500 | 2,500 | 500 | 2,500 |
| Average particle size(μm) | | | | |
| Encapsulated oil droplet | 0.5 | 0.5 | 10 | not obtained |
| Microcapsule | 100 | 50 | 500 | not obtained |
| Inner oil phase capsulating rate(%) | 100 | 100 | 70 | — |
| Shearing-resistance | ◯ | ◯ | X | — |

While the encapsulated oil droplet diameter in Examples was substantially the same as the emulsified particle size at the time of preparing the O/W emulsion, the encapsulated oil droplet diameter in Comparative Examples increased up to 10 μm.

Also, no loss in the inner oil phase occurred in Examples. By contrast, in Comparative Examples, loss in the inner oil phase was remarkable and no O/W/O emulsion was obtained under a severer condition.

Further, the microcapsules of Examples were excellent in shearing-resistance and maintained substantially 100% of the inner oil phase capsulating rate.

As in the foregoing, as well as the case of the immediately-releasing microcapsule mentioned above, the emulsifying condition in the making of the gradually-releasing microcapsule can be set freely, whereby the particle size of microcapsule can be controlled easily. Also, the inner oil phase capsulating rate is high and yields no loss at the time of making.

The microcapsules of TABLE 7 were prepared using the following ingredients according to the making method in Test Example I-2

(Example Microcapsule)

| Inner oil phase: | |
|---|---|
| (1)Vitamin A palmitate | 5 wt % |
| (2)Cetyl isooctanoate | 5 |
| Water phase: | |
| (3)POE(60) hardened caster oil | 0.5 |
| (4)Glycerin | 10 |
| (5)Agar(PS-84) | 1.5 |
| (6)Ion-exchanged water | 28 |
| Outer oil phase: | |
| (7)POE methylpolysiloxane copolymer | 0.5 |
| (8)Dimethylpolysiloxane(6 cps) | 49.5 |
| Total | 100.0 |

(Comparative Example Microcapsule)

| Inner oil phase: | |
|---|---|
| (1)Stearic acid | 2 wt % |
| (2)Squalane | 10 |
| Water phase: | |
| (3)Sorbitan monooleate | 2 |
| (4)Glycerin | 5 |
| (5)Agar(PS-84) | 1.5 |
| (6)Ion-exchanged water | 29.5 |
| Outer oil phase: | |
| (7)POE methylpolysiloxane copolymer | 0.5 |
| (8)Dimethylpolysiloxane(6 cps) | 49.5 |
| Total | 100.0 |

Test Example II-3

| Inner oil phase: | |
|---|---|
| (1)Vitamin A palmitate | 5 wt % |
| (2)Squalane | 9.5 |
| Water phase: | |
| (3)POE(60) hardened caster oil | 0.5 |
| (4)1,3-Butylenegrycol | 10 |
| (5)Carrageenan | 2 |
| (6)Ion-exchanged water | 23 |
| Outer oil phase: | |
| (7)POE methylpolysiloxane copolymer | 1 |
| (8)Dimethylpolysiloxane(6 cs) | 48 |
| (9)Benton 38 | 1 |
| Total | 100.0 |

(Preparation Method)

With the above Ingredients, a microcapsule oily dispersion was obtained according to Test Example I-3.

The average particle size of the microcapsule and the encapsulated oil droplet were 10 μm and 0.5 μm, respectively. Also, the inner oil phase capsulating rate was 100%. Further, the fracture strength of the microcapsule was 1,500 g/cm$^2$.

Compounding Example II-1 O/W Cream
(Microcapsule Ingredients)

TABLE 8

| Ingredients | Microcapsule 1 | Microcapsule 2 |
|---|---|---|
| Inner oil phase: | | |
| Cyclosporin | 5 | — |
| Crotamiton | 15 | — |
| Vitamin C dipalmitate | — | 2.5 |
| Dioctyl sebacate | — | 15 |
| Water phase: | | |
| 1,3-Butylene glycol | 10 | 10 |
| POE(60) hardened caster oil | 1 | 1 |
| Agar(S-5) | 1.5 | 1.5 |
| Ion-exchanged water | 17.5 | 20 |
| Outer oil phase: | | |
| POE methylpolysiloxane copolymer | 1 | 1 |
| Octamethylcyclotetrasiloxane | 49 | 49 |

(Microcapsule Preparation Method)

With the ingredients of TABLE 8, a microcapsule oily dispersion was prepared according to Test Example II-2 and filtrated to obtain Microcapsules. The fracture strength of Microcapsules 1 and 2 were 1,080 and 1,100 g/cm$^2$, respectively.

(Cream Preparation)

With the ingredients of TABLE 9, O/W creams were prepared by a normal method. They were stored at 0° C., room temperature, and 50° C., and whether crystals deposited or not were observed by the naked eye with time until 1 month thereafter. Results are shown in TABLE 9.

TABLE 9

| Ingredients | Cream | | | |
|---|---|---|---|---|
| | A | B | C | D |
| Stearyl alcohol | 6 | 6 | 6 | 6 |
| Stearic acid | 2 | 2 | 2 | 2 |
| Hydrogenated lanolin | 4 | 4 | 4 | 4 |
| Squalane | 9 | 9 | 3 | 3 |
| Octyldodecanol | 10 | 10 | 10 | 10 |
| Cyclosporin | — | — | 2 | — |
| Crotamiton | — | — | 6 | — |
| Vitamin C dipalmitate | — | — | — | 1 |
| Dioctyl sebacate | — | — | — | 6 |
| 1,3-Butylene glycol | 6 | 6 | 6 | 6 |
| PEG 1500 | 4 | 4 | 4 | 4 |
| POE(25) cetyl alcohol | 3 | 3 | 3 | 3 |
| Glyceryl monostearate | 2 | 2 | 2 | 2 |
| Purified water | 34 | 34 | 52 | 53 |
| Microcapsule 1 | 20 | — | — | — |
| Microcapsule 2 | — | 20 | — | — |
| Antiseptic | Q.S. | Q.S. | Q.S. | Q.S. |
| Antioxidant | Q.S. | Q.S. | Q.S. | Q.S. |
| Crystal deposit (0° C. × 3 days) | none | none | exist | exist |
| (0° C. × 1 month) | none | none | exist | exist |
| (r.t. × 2 weeks) | none | none | exist | exist |
| (r.t. × 1 month) | none | none | exist | exist |
| (50° C. × 2 weeks) | none | none | none | none |
| (50° C. × 1 month) | none | none | exist | exist |

In the case where a microcapsule encapsulating easy-to-crystallize drugs such as cyclosporin or vitamin C dipalmitate was compounded as with Creams A and B, no crystal deposition was seen at all.

Therefore, the microcapsule of the present invention is very stable, whereby using it can realize a product which can stably contain drugs that have conventionally been hard to be compounded and gradually releases these drugs when applied on skin.

Also, a large amount of water-soluble drugs can be stably encapsulated in the water phase, whereby the microcapsule of the present invention is useful for preparation in which water-soluble drugs have conventionally been hardly compounded.

Compounding Example II-2 Lipstick (Microcapsule Ingredients)

| Inner oil phase: | |
|---|---|
| Retinol | 5 wt % |
| Dioctyl sebacate | 15 |
| Water phase: | |
| 1,3-Butylene glycol | 10 |
| POE(60) hardened caster oil | 1 |
| Agar(M-7) | 1.5 |
| Ascorbic acid 2-glucoside | 5 |
| Ion-exchanged water | 12.5 |
| Outer oil phase: | |
| POE methylpolysiloxane copolymer | 1 |
| Octamethylcyclotetrasiloxane | 49 |

(Microcapsule Preparation Method)

With the above ingredients, a microcapsule oily dispersion was prepared according to Test Example II-2, and then filtrated to obtain microcapsules (fracture strength of the microcapsule: 1,400 g/cm²).

(Lipstick Preparation and Durability Test)

TABLE 10

| Ingredients | Lipstick A | Lipstick B |
|---|---|---|
| Titanium dioxide | 5 | 5 |
| Red #201 | 0.6 | 0.6 |
| Red #202 | 1 | 1 |
| Red #223 | 0.2 | 0.2 |
| Candelilla wax | 9 | 9 |
| Solid paraffin | 8 | 8 |
| Bees wax | 5 | 5 |
| Carnauba wax | 5 | 5 |
| lanolin | 11 | 11 |
| Caster oil | 5.2 | 17.2 |
| Cetyl 2-ethylhexanoate | 20 | 20 |
| Isopropyl myristate | 10 | 10 |
| Microcapsule | 20 | — |
| Ion-exchanged water | — | 5 |
| Glycerin | — | 2 |
| POE(25)POP(20)2-tetradecyl ether | — | 1 |
| Antioxidant | Q.S. | Q.S. |
| Perfume | Q.S. | Q.S. |
| Moisturizing effect | ◎ | Δ |
| Wrinkle-improvement effect | ◎ | X |

Lipsticks were prepared by a normal method with the ingredients of TABLE 10. A using test for lipsticks was conducted by 20 special panels, and durability of moisturizing and wrinkle-improvement effects was asked, whereby the evaluation was performed according to the following standard.

Evaluating Standard:

◎: 16 or more panels answered that there was durability.

○: 11 to 15 panels answered that there was durability.

Δ: 6 to 10 panels answered that there was durability.

X: 5 or less panels answered dial there was durability.

In normal lipsticks, easy-to-oxidize drugs such as retinol have been hard to be compounded due to their formulations, and also water-soluble humectants such as ascorbic acid derivatives and the like cannot be compounded (Lipstick B).

On the other hand, if the microcapsule of the present invention is used as Lipstick A, such drugs can be stably compounded in lipsticks, whereby those having durability of moisturizing and wrinkle-improvement effects are obtained.

Compounding Example II-3 Check Rouge

TABLE 11

| Ingredients | Cheek rouge A | Cheek rouge B |
|---|---|---|
| Kaoline | 20 | 20 |
| Titanium dioxide | 4.2 | 4.2 |
| Iron oxide(red) | 0.3 | 0.3 |
| Red #202 | 0.5 | 0.5 |
| Ceresine | 15 | 15 |
| Liquid paraffin | 15 | 25 |
| Isopropyl myristate | 5 | 15 |
| Microcapsule(Compounding Example II-2) | 20 | — |
| Antioxidant | Q.S. | Q.S. |
| Perfume | Q.S. | Q.S. |
| Moisturizing effect | ◎ | X |
| Wrinkle-improvement effect | ◎ | X |

With the ingredients of TABLE 11, solid check rouges were prepared by a normal method. The Check rouge A including microcapsule had high durability of moisturizing and wrinkle-improvement effects.

Compounding Example II-4 O/W Foundation

TABLE 12

| Ingredients | Foundation A | Foundation B |
|---|---|---|
| Talc | 3 | 3 |
| Titanium dioxide | 5 | 5 |
| Bentonite | 0.5 | 0.5 |
| Microcapsule* | 10 | — |
| POE sorbitan monostearate | 0.9 | 0.9 |
| Triethanolamine | 1 | 1 |
| Propylene glycol | 10 | 10 |
| Vitamin E acetate | — | 1 |
| Ion-exchanged water | 48.4 | 57.4 |
| Stearic acid | 2.2 | 2.2 |
| Isohexadecyl alcohol | 7 | 7 |
| Glyceryl monostearate | 2 | 2 |
| Liquid lanolin | 2 | 2 |
| Liquid paraffin | 8 | 8 |
| Antiseptic | Q.S. | Q.S. |
| Antioxidant | Q.S. | Q.S. |
| Perfume | Q.S. | Q.S. |
| Change of color(50° C., 1 month) | none | exist |

*It was prepared according to the microcapsule of Compounding Example II-2 woth vitamin E acetate in the place of retinol.

O/W foundations were prepared by a normal method, and whether there was a change of color or not after being stored for 1 month at 50° C. was observed with the naked eye.

Although a change of color was seen in Foundation B in which vitamin E acetate was compounded as it was, no change of color was seen in Foundation A in which a microcapsule encapsulating vitamin E acetate was compounded.

Compounding Example II-5 Jelly-like Peel-off Pack

| | |
|---|---|
| Polyvinyl alcohol | 15 wt % |
| Carboxymethyl cellulose | 5 |
| 1,3-Butylene glycol | 5 |
| Ethanol | 5 |
| POE oleyl alcohol | 0.5 |
| Microcapsule(Compounding Example II-2) | 10 |
| Ion-exchanged water | 59.5 |

Jelly-like peel-off pack was prepared by a normal method. Since normal jelly-like packs are aqueous, oils and oil-soluble drugs are hard to be compounded therein. By contrast, using the microcapsule of the present invention can yield a pack which can stably contain oils and oil-soluble drugs therein, and gradually release these encapsulated materials therefrom upon application.

Compounding Example II-6 Capsule-containing Sheet

| | |
|---|---|
| (1)1,3-Butylene glycol | 15 wt % |
| (2)Polyvinyl alcohol | 5 |
| (3)Microcapsule(Compounding Example II-2) | 50 |
| (4)Ethanol | 10 |
| (5)PEG 6000 | 3 |
| (6)PEG 1200 | 2 |
| (7)POE(25) hardened caster oil | 5 |
| (8)Stearic acid | 10 |

(Preparation Method)

According to Compounding Example I-6, a sheet type product was prepared.

Compounding Example II-7 Deodorant Powder Spray (Microcapsule Ingredients)

| | |
|---|---|
| Inner oil phase: | |
| (1) Zinc paraphenolsulfonate | 4.25 wt % |
| (2) Squalane | 4 |
| (3) Triclosan | 0.25 |
| (4) Isopropyl myristate | 2.5 |
| Water phase: | |
| (5) 1,3-Butylene glycol | 10 |
| (6) POE(60) hardened caster oil | 1 |
| (7) Agar(T-1) | 1 |
| (8) Gellan gum | 0.3 |
| (9) Citric acid | Q.S. |
| (10)Sodium chloride | 0.1 |
| (11)Ascorbic acid 2-glucoside | 2.5 |
| (12)Ion-exchanged water | Balance |
| (13)Antioxidant | Q.S. |
| Outer oil phase: | |
| (14)POE methylpolysiloxane copolymer | 1 |
| (15)Octadecylcyclotetrasiloxane | 49 |

(Preparation Method)

With the above ingredients, microcapsules were obtained according to Compounding Example I-7 (fracture strength of the microcapsule: 800 g/cm$^2$). by using the microcapsules, a spray was obtained according to Compounding Example I-7.

Compounding Example II-8 Semitransparent Lotion

| | |
|---|---|
| (1)1,3-Butylene glycol | 6 wt % |
| (2)Glycerin | 5 |
| (3)Polyethylene glycol 400 | 3 |
| (4)Olive oil | 0.5 |
| (5)POE(20) sorbitan monostearate | 1.5 |
| (6)Ethanol | 5 |
| (7)Microcapsule(ExampleII-1) | 5.3 |
| (8)Purified water | 73.7 |
| (9)Perfume | Q.S. |
| (10)Antiseptic | Q.S. |

(Preparation Method)

A lotion was obtained according to Compounding Example I-8.

Compounding Example II-9 O/W Emollient Lotion

| | |
|---|---|
| (1)Stearic acid | 2 wt % |
| (2)Cetyl alcohol | 1.5 |
| (3)Vaseline | 4 |
| (4)Squalane | 5 |
| (5)Glyceryl tri-2-ethylhexanoate | 2 |
| (6)Sorbitan monooleate | 2 |
| (7)Dipropylene glycol | 5 |
| (8)Polyethylene glycol 1500 | 3 |
| (9)Triethanolamine | 1 |
| (10)Microcapsule(Example II-2, oily dispersion) | 10 |
| (11)Purified water | 64.5 |
| (12)Perfume | Q.S. |
| (13)Antiseptic | Q.S. |

(Preparation Method)

An emollient lotion was obtained according to Compounding Example I-9.

Compounding Example II-10 W/O Massage Cream

| (1)Microcrystalline wax | 9 wt % |
|---|---|
| (2)Solid paraffin | 2 |
| (3)Bees wax | 3 |
| (4)Vaseline | 5 |
| (5)Hydrogenated lanolin | 5 |
| (6)Squalane | 30 |
| (7)Hexadecyl adipate | 1 |
| (8)Propylene glycol | 5 |
| (9)Glyceryl monooleate | 3.5 |
| (10)POE(20) sorbitan monooleate | 1 |
| (11)Microcapsule(Example II-2, oily dispersion) | 4 |
| (12)Purified water | 30.5 |
| (13)Perfume | Q.S. |
| (14)Antiseptic | Q.S. |

(Preparation Method)

A cream was obtained according to Compounding Example I-10.

Compounding Example II-11 W/O Emollient Cream

| (1)Squalane | 20 wt % |
|---|---|
| (2)Cetyl isooctanoate | 8.5 |
| (3)Microcrystalline wax | 1 |
| (4)Organophilic clay mineral | 1.3 |
| (5)POE glyceryl triisostearate | 0.2 |
| (6)Glycerin | 5 |
| (7)Microcapsule(Example II-1, oily dispersion) | 5 |
| (8)Purified water | 59 |
| (9)Perfume | Q.S. |
| (10)Antiseptic | Q.S. |

(Preparation Method)

A cream was obtained according to Compounding Example I-11.

Compounding Example II-12 Moisture Gel

| (1)Dipropylene glycol | 7 wt % |
|---|---|
| (2)Polyethylene glycol 1500 | 8 |
| (3)Carboxyvinyl polymer | 0.4 |
| (4)Methyl cellulose | 0.2 |
| (5)POE(15) oleyl ether | 1 |
| (6)Potassium hydroxide | 0.1 |
| (7)Microcapsule(Example II-1) | 1 |
| (8)Purified water | 82.3 |
| (9)Perfume | Q.S. |

(Preparation Method)

A gel was obtained according to Compounding Example I-12.

III. Non-Releasing Microcapsule

Test Example III-1

Microcapsules were prepared in the same way as Test Example I-1 mentioned above except for using agar in TABLE 13 as a gelling agent. The shearing-resistance and fracture strength of the microcapsules were studied. Also, the maintaining characteristic of encapsulated oil droplets was examined according to the following method.
(Maintaining Test)

The microcapsule oily dispersion and an ethanol solution containing 5% fragrance (control) were put on the inside of left and right wrists by 0.1 g each with a spatula, respectively. Whether the scent (fragrance scent) was felt or not was evaluated before being spread (shown as "before"), immediately after being spread with a finger tip (shown as "after"), and 3 hours thereafter according to the following standard:

Evaluation Standard

○: substantially no scent was felt.

X: scent was felt.

TABLE 13

| | Agar | | Fracture | Shearing- | Maintaining test | | |
|---|---|---|---|---|---|---|---|
| No. | Name | Amount | strength | resistance | Before | After | 3 hr |
| 1 | AX-100 | 0.7% | 5 g/cm² | X | ○ | X | X |
| 2 | AX-200 | 1.5 | 400 | ○ | ○ | X | X |
| 3 | PS-84 | 1.5 | 1,323 | ○ | ○ | X | X |
| 4 | PS-84 | 3.0 | 2,274 | ○ | ○ | ○ | ○ |
| 5 | M-7 | 3.0 | 3,500 | ○ | ○ | ○ | ○ |
| 6 | M-7 | 5.0 | 4,500 | ○ | ○ | ○ | ○ |
| Control | — | | — | | X | X | X |

The shearing-resistance was insufficient in Sample 1. In Samples 2 and 3, while the shearing-resistance was favorable, the scent was felt by releasing the perfume by application.

In Samples 4 to 6, by contrast, the scent was hardly felt after application, whereby it was suggested that the perfume was maintained in the microcapsule without being released.

Therefore, for exhibiting a shearing-resistance and a maintaining characteristic of encapsulated oil droplets, it is preferred that the fracture strength of the microcapsule is at least 2,000 g/cm² but 5,000 g/cm² or less, and is 2,200 to 4,500 g/cm² in particular.

Test Example III-2

Microcapsules prepared by use of a two-stage emulsifying method (Examples III-1, III-2) and those prepared by a conventional method (Comparative Examples III-1, III-2) were compared with each other. In each case, the average particle size of O/W emulsion was set to 0.5 μm. The fracture strength of each gel prepared with a water phase was 2,300 g/cm². Results are shown in TABLE 14.

TABLE 14

| | Ex. III-1 | Ex. III-2 | Comp.Ex. III-1 | Comp.Ex III-2 |
|---|---|---|---|---|
| O/W/O emulsifying condition | | | | |
| Temperature(° C.) | 50 | 70 | 50 | 70 |
| Stirring rate(rpm) | 500 | 2,500 | 500 | 2,500 |
| Average particle size(μm) | | | | |
| Encapsulated oil droplet | 0.5 | 0.5 | 10 | not obtained |
| Microcapsule | 100 | 50 | 500 | not obtained |
| Inner oil phase capsulating rate(%) | 100 | 100 | 70 | — |
| Shearing-resistance | ○ | ○ | X | — |

While the encapsulated oil droplet diameter in Examples was substantially the same as the emulsified particle size at the time of preparing the O/W emulsion, the encapsulated oil droplet diameter in Comparative Examples increased up to 10 μm.

Also, no loss in the inner oil phase occurred in Examples. By contrast, in Comparative Examples, loss in the inner oil phase was remarkable and no O/W/O emulsion was obtained under a severer condition.

Further, the microcapsules of Examples were excellent in shearing-resistance and maintained substantially 100% of the inner oil phase capsulating rate.

As in the foregoing, as well as the case of the immediately- or gradually-releasing microcapsules mentioned above, the emulsifying condition in the making of the non-releasing microcapsule can be set freely, whereby the particle size of microcapsule can be controlled easily. Also, the inner oil phase capsulating rate is high and yields no loss at the time of making.

The microcapsules of TABLE 14 were prepared using the following ingredients according to the making method in Test Example I-2

(Example Microcapsule)

| Inner oil phase: | |
|---|---|
| (1)Vitamin A palmitate | 5 wt % |
| (2)Cetyl isooctanoate | 5 |
| Water phase: | |
| (3)POE(60) hardened castor oil | 0.5 |
| (4)Glycerin | 10 |
| (5)Agar(PS-84) | 3 |
| (6)Ion-exchanged water | 26.5 |
| Outer oil phase: | |
| (7)POE methylpolysiloxane copolymer | 0.5 |
| (8)Dimethylpolysiloxane(6 cps) | 49.5 |
| Total | 100.0 |

(Comparative Example Microcapsule)

| Inner oil phase: | |
|---|---|
| (1)Stearic acid | 2 wt % |
| (2)Squalane | 10 |
| Water phase: | |
| (3)Sorbitan monooleate | 2 |
| (4)Glycerin | 5 |
| (5)Agar(PS-84) | 3 |
| (6)Ion-exchanged water | 28 |
| Outer oil phase: | |
| (7)POE methylpolysiloxane copolymer | 0.5 |
| (8)Dimethylpolysiloxane(6 cps) | 49.5 |
| Total | 100.0 |

Test Example III-3

| Inner oil phase: | |
|---|---|
| (1)Vitamin A palmitate | 5 wt % |
| (2)Squalane | 9.5 |
| Water phase: | |
| (3)POE(60) hardened castor oil | 0.5 |
| (4)1,3-Butylenegrycol | 10 |
| (5)Carrageenan | 5 |
| (6)Ion-exchanged water | 20 |

| -continued | |
|---|---|
| Outer oil phase: | |
| (7)POE methylpolysiloxane copolymer | 1 |
| (8)Dimethylpolysiloxane(6 cs) | 48 |
| (9)Benton 38 | 1 |
| Total | 100.0 |

(Preparation Method)

A microcapsule oily dispersion was obtained according to Test Example I-3.

The average particle size of the microcapsule and the encapsulated oil droplet were 10 $\mu$m and 0.5 $\mu$m, respectively. Also, the inner oil phase capsulating rate was 100%. Further, the fracture strength of the microcapsule was 2,400 g/cm$^2$.

Compounding Example III-1 O/W Foundation
(Microcapsule Ingredients)

| Inner oil phase: | |
|---|---|
| 4-Tert-butyl-4'-methoxybenzoylmethane | 5 wt % |
| Dioctyl sebacate | 15 |
| Water phase: | |
| 1,3-Butylene glycol | 10 |
| POE(60) hardened castor oil | 1 |
| Agar(M-7) | 3 |
| Ascorbic acid 2-glucoside | 5 |
| Ion-exchanged water | 11 |
| Outer oil phase: | |
| POE methylpolysiloxane copolymer | 1 |
| Octamethylcyclotetrasiloxane | 49 |

(Microcapsule Preparation Method)

In the same way as Test Example III-1, a microcapsule oily dispersion was prepared and filtrated to obtain microcapsules (fracture strength: 3,500 g/cm$^2$).

(Foundation Preparation)

An O/W foundation was prepared by a normal method, and whether there was a change of color or not after being stored for 1 month at 50° C. was observed with the naked eye.

As shown in TABLE 15, although a change of color was seen in Foundation B in which an organic UV-absorbing agent (4-tert-butyl-4'-methoxybenzoylmethane) was compounded simply, no change of color was seen in Foundation A in which a microcapsule encapsulating the organic UV-absorbing agent was compounded.

Therefore, the microcapsule of the present invention is excellent in store stability of the encapsulated oil droplets. Also, as shown in Test Example III-1, since the encapsulated oil droplets were maintained in the microcapsule even after application, it can prevent the UV-absorbing agent from contacting with skin directly.

TABLE 15

| Ingredients | Foundation A | Foundation B |
|---|---|---|
| Talc | 3 | 3 |
| Titanium dioxide | 5 | 5 |
| Bentonite | 0.5 | 0.5 |
| Microcapsule | 10 | — |

TABLE 15-continued

| Ingredients | Foundation A | Foundation B |
|---|---|---|
| POE sorbitan monostearate | 0.9 | 0.9 |
| Triethanolamine | 1 | 1 |
| Propylene glycol | 10 | 10 |
| Diisopropyl sebacate | — | 10 |
| 4-Tert-butyl-4'-methoxybenzoylmethane | — | 1 |
| Ion-exchanged water | 48.4 | 47.4 |
| Stearic acid | 2.2 | 2.2 |
| Isohexadecyl alcohol | 7 | 7 |
| Glyceryl monostearate | 2 | 2 |
| Liquid lanolin | 2 | 2 |
| Liquid paraffin | 8 | 8 |
| Antiseptic | Q.S. | Q.S. |
| Antioxidant | Q.S. | Q.S. |
| Perfume | Q.S. | Q.S. |
| Change of color(50° C., 1 month) | none | exist |

Compounding Example III-2 W/O Sunscreen Cream

In TABLE 16, as well as Compounding Example III-1, although a change of color was seen in Sunscreen cream B in which an organic UV-absorbing agent (4-tert-butyl-4'-methoxybenzoylmethane) was compounded simply, no change of color was seen in Sunscreen cream Foundation A in which a microcapsule encapsulating the organic UV-absorbing agent was compounded.

TABLE 16

| Ingredients | Cream A | Cream B |
|---|---|---|
| 1,3-Butylene glycol | 5 | 5 |
| Microcapsule(Compounding Example III-1) | 20 | — |
| Ion-exchanged water | 19.5 | 37.5 |
| Octyl p-methoxycinnamate | 5 | 5 |
| 4-Tert-butyl-4'-methoxybenzoylmethane | — | 2 |
| Oxybenzone | 3 | 3 |
| Hydrophobic-treated titanium dioxide | 3 | 3 |
| Squalane | 40 | 40 |
| Glyceryl diisostearate | 3 | 3 |
| Organophilic montmorillonite | 1.5 | 1.5 |
| Antiseptic | Q.S. | Q.S. |
| Perfume | Q.S. | Q.S. |
| Change of color (50° C., 1 month) | none | exist |

Compounding Example III-3 Lipstick

| | | |
|---|---|---|
| Titanium dioxide | 5 | wt % |
| Red #201 | 0.6 | |
| Red #202 | 1 | |
| Red #223 | 0.2 | |
| Candelilla wax | 9 | |
| Solid paraffin | 8 | |
| Bees wax | 5 | |
| Carnauba wax | 5 | |
| lanolin | 11 | |
| Caster oil | 5.2 | |
| Cetyl 2-ethylhexanoate | 20 | |
| Isopropyl myristate | 10 | |
| Microcapsule(Compounding Example III-1) | 20 | |
| Antioxidant | Q.S. | |
| Perfume | Q.S. | |

Compounding Example III-4 Check Rouge

| | | |
|---|---|---|
| Kaoline | 20 | wt % |
| Titanium dioxide | 4.2 | |
| Iron oxide (red) | 0.3 | |
| Red #202 | 0.5 | |
| Ceresine | 15 | |
| Liquid paraffin | 15 | |
| Isopropyl myristate | 5 | |
| Microcapsule(Compounding Example III-1) | 20 | |
| Antioxidant | Q.S. | |
| Perfume | Q.S. | |

Compounding Example III-5 Facial Scrub Soap (Microcapsule Ingredients)

| | | |
|---|---|---|
| Inner oil phase: | | |
| Squalane | 3 | wt % |
| Water phase: | | |
| 1,3-Butylene glycol | 10 | |
| POE(60) hardened caster oil | 1 | |
| Agar(M-7) | 5 | |
| Ion-exchanged water | 31 | |
| Outer oil phase: | | |
| POE methylpolysiloxane copolymer | 1 | |
| Decamethylcyclopentasiloxane | 49 | |

(Microcapsule Preparation Method)

In the same way as Test Example III-1, a microcapsule oily dispersion was prepared and filtrated to obtain microcapsule (fracture strength: 5,000 g/cm²).

(Facial Scrub Soap Preparation)

| | | |
|---|---|---|
| Part A: | | |
| Stearic acid | 12 | wt % |
| Myristic acid | 14 | |
| Lauric acid | 5 | |
| Squalane | 3 | |
| Sorbit (70% sorbitol aqueous solution) | 15 | |
| Glycerin | 10 | |
| 1,3-Butylene glycol | 10 | |
| Part B: | | |
| Potassium hydroxide | 5 | |
| Ion-exchanged water | 15 | |
| Part C: | | |
| POE(20) glyceryl monostearate | 2 | |
| Acyl methyltaurine | 4 | |
| Part D: | | |
| Microcapsule | 5 | |

Preparation method:

Part A was dissolved with beating and maintained at 70° C. Part B was added to the part A while being stirred and the mixture was neutralized sufficiently. Part C was added to the mixture at 50° C., and then part D was further added and mixed therein. The mixture was deaerated, filtrated and cooled to obtain a facial scrub soap.

IV. Coated Microcapsule

Test Example IV-1

(Non-Coated Microcapsule Ingredients)

| Inner oil phase: | |
|---|---|
| Squalane | 10 wt % |
| Water phase: | |
| 1,3-Butylene glycol | 5 |
| POE(60) hardened caster oil | 1 |
| Agar(PS-84) | 1 |
| Ascorbic acid 2-glucoside | 2 |
| Ion-exchanged water | 31 |
| Outer oil phase: | |
| POE methylpolysiloxane copolymer | 1 |
| Octamethylcyclotetrasiloxane | 49 |

(Non-Coated Microcapsule Preparation Method)

The inner oil phase was gradually added to a mixture of 1,3-butylene glycol, POE (60) hydrogenated castor oil and ascorbic acid 2-glucoside to obtain an oil-in-water-soluble-solvent type emulsion. Agar was dissolved in ion-exchanged water with heating at 90° C. to prepare an aqueous agar solution. The aqueous agar solution cooled to 50° C. was added to the oil-in-water-soluble-solvent type emulsion heated to 50° C. while being stirred, whereby an O/W emulsion (average particle size: 0.5 μm) was obtained.

The O/W emulsion was added to the outer oil phase, and the mixture was emulsified at 50° C.×500 rpm to prepare an O/W/O emulsion. It was gradually cooled to room temperature to harden agar in the water phase, thereby obtaining a microcapsule oily dispersion (average microcapsule particle size: 100 μm; average encapsulated oil droplet particle size: 0.5 μm). This oily dispersion was filtrated to obtain non-coated microcapsules.

(Coated Microcapsule)

A coating agent was dissolved in the above-mentioned microcapsule oily dispersion with a predetermined concentration. After being stirred for 30 minutes, the resulting was filtrated, thereby obtaining coated microcapsules.

(Contraction State)

The respective states immediately after filtration and after being dried for 24 hours at 25° C. were observed through a microscope, and were evaluated according to the following standard:

Evaluation Standard:
  o: no contraction
  Δ: slight contraction
  X: obvious contraction (Elution of A2G)

10 weight parts of the microcapsule were dispersed into 90 weight parts of water, and the dispersion was stored at room temperature. The coated microcapsule dried for 24 hours at 25° C. after filtration, and the non-coated microcapsule immediately after filtration were tested. After 1 month, ascorbic acid 2-glucoside (A2G) in water was quantitatively determined by HPLC. The eluting ratio of A2G was calculated while the case where A2G was wholly eluted from the microcapsule was taken as 100%.

(Dispersibility)

10 weight parts of the microcapsule were added to 90 weight parts of a dispersion medium. After being stirred for 10 minutes, the resulting mixture was observed through a microscope, and was evaluated according to the following standard. The coated microcapsule dried for 24 hours at 25° C. after filtration, and the non-coated microcapsule immediately after filtration were tested.

Evaluation Standard:
  ⊙: no coagulation at all
  o: slight coagulation
  Δ: half or more coagulated
  X: substantially coagulated

TABLE 17

| Coating agent* | | | | |
|---|---|---|---|---|
| Solid paraffin | 5 | — | — | — |
| Highly polymerized methyl polysiloxane | — | 2 | — | — |
| Ethyl cellulose | — | — | 1 | — |
| Contraction State | | | | |
| Immediately after filtrating | o | o | o | o |
| After drying | o | o | o | X |
| Elution of A2G(%) | 0 | 0 | 0 | 10 |
| Dispersibility | | | | |
| Methylpolysiloxane(20 cps) | ⊙ | ⊙ | o | Δ |
| Dioctyl sebacate | o | o | ⊙ | Δ |

*Adding amount (g) of the coating agent per 100 g of microcapsule oily dispersion TABLE 17 shows results of evaluation of microcapsules coated with lipophilic coating agents (solid paraffin, highly polymerized methyl polysiloxane) or an amphiphilic coating agent (ethyl cellulose). From TABLE 17, it can be seen that these coatings suppress the contraction of microcapsules in air, and improve the dispersibility in lipophilic medium. Also, the elution of encapsulated component (ascorbic acid 2-glucoside) from the microcapsule in water is suppressed.

When a non-coated microcapsule is simply added into base materials containing lipophilic and amphiphilic substances, the microcapsule does not be coated sufficiently, whereby the effects mentioned above would not be exhibited. This will be supported by the following results.

TABLE 18 shows the dispersibility when coated or non-coated microcapsules are dispersed into a medium containing a coating agent. When TABLE 18 is compared with TABLE 17, no difference in dispersibility is seen according to whether there is a coating agent in the medium or not. In any case, the coated microcapsule has a higher dispersibility than the non-coated microcapsule. As a consequence, it is understood that, for coating a microcapsule, it is necessary to bring the microcapsule into contact with a coating agent, then eliminate the solvent, and dry the residue; and that coating would not sufficiently be effected when the microcapsule is simply added in a base material containing a coating agent.

TABLE 18

| Coating agent* | | | | |
|---|---|---|---|---|
| Solid paraffin | 5 | — | — | — |
| Highly polymerized methyl polysiloxane | — | 2 | — | — |
| Methyl cellulose | — | — | 1 | — |
| Dispersibility** | | | | |
| Octyl sebacate containing solid paraffin | o | o | ⊙ | Δ |
| Methyl polysiloxane(20 cps) containing highly polymerized methyl polysiloxane | ⊙ | ⊙ | o | Δ |
| Octyl sebacate containing ethyl cellulose | o | o | ⊙ | Δ |

*Adding amount (g) of the coating agent per 100 g of microcapsule oily dispersion
**Each concentration of coating agent in dispersion medium was 10 wt %

Test Example IV-2

The case where non-coated microcapsules of Test Example IV-1 were subjected to hydrophilic coating was studied similarly. Results are shown in TABLE 19.

From TABLE 19, it is understood that the contraction in air and the elution of encapsulated components from the microcapsule are suppressed in the case of hydrophilic coating as well. Also, the dispersibility of microcapsule in water can be improved by hydrophilic coating. Here, substantially no difference was seen in dispersibility between the case where each microcapsule was dispersed in water and the case where it was dispersed in water containing a hydrophilic coating agent.

TABLE 19

| Coating agent* Polyvinyl alcohol | 5 | 1 | — |
|---|---|---|---|
| Contraction State | | | |
| Immediately after filtrating | ○ | ○ | ○ |
| After drying | ○ | Δ | X |
| Elution of A2G(%) | 0 | 5 | 10 |
| Dispersibility | | | |
| Water | ⊚ | ⊚ | ○ |
| Water containing polyvinyl alcohol** | ⊚ | ⊚ | ○ |

*Adding amount (g) of the coating agent per 100 g of microcapsule oily dispersion
**The concentration of polyvinyl alcohol in water was 10 wt %.

Manufacturing Example IV-1

Non-coated microcapsules were prepared by using Ina Agar AX-100 in the place of agar in the non-coated microcapsule of Test Example IV-1, and collected by filtration. 10 g of this obtained microcapsules were added to a mixture of 10 g of siliconized pullulan, 60 g of decamethylcylcopentasiloxane, and 30 g of ethanol. After being stirred for 1 minute, the microcapsules were collected by filtration, and dried upon blowing at room temperature, whereby the aimed coated microcapsules were obtained.

Manufacturing Example IV-2

Non-coated microcapsules were prepared by using carrageenan in the place of agar in the non-coated microcapsule of Test Example IV-1, and collected by filtration. 10 g of thus obtained microcapsules were added to a mixture of 5 g of polyvinyl alcohol, 5 g of acrylic acid-alkyl acrylate copolymer, 70 g of purified water, and 20 g of ethanol. After being stirred for 10 minutes, the microcapsules were collected by filtration, and dried upon blowing at room temperature, whereby the aimed coated microcapsules were obtained.

Manufacturing Example IV-3

10 g of non-coated microcapsules of Test Example IV-1 were added to a mixture of 5 g of stearic acid, 5 g of POE hardened caster oil, 60 g of hexane, and 30 g of ethanol. After being stirred for 5 minutes, the microcapsules were collected by filtration, and dried upon blowing at room temperature, whereby the aimed coated microcapsules were obtained.

Compounding Example IV-1 O/W Cream

| Stearic acid | 8 wt % |
|---|---|
| Stearyl alcohol | 4 |
| Propylene glycol | 5 |
| Glyceryl monostearate | 2 |

-continued

| Potassium hydroxide | 0.4 |
|---|---|
| Coated microcapsule(Manufacturing Example IV-1) | 10 |
| Purified water | 64.6 |
| Antiseptic | Q.S. |
| Antioxidant | Q.S. |
| Perfume | Q.S. |

(Preparation Method)

Propylene glycol and potassium hydroxide were added to purified water, and then heated to 70° C. (water phase). Stearic acid and stearyl alcohol were dissolved with heating, and then, with glyceryl monostearate, antiseptic, antioxidant and perfume added thereto, were heated to 70° C. (oil phase). The oil phase was added to the water phase and pre-emulsified. The emulsion was mixed uniformly by a homomixer, and further mixed uniformly at room temperature with the microcapsule added thereto to obtain an O/W cream.

Compounding Example IV-2 W/O Cream

| Squalane | 20 wt % |
|---|---|
| Cetyl isooctanoate | 8.5 |
| Microcrystalline wax | 1 |
| Organophilic clay mineral | 1.3 |
| POE glyceryl triisostearate | 0.2 |
| Glycerin | 10 |
| Coated microcapsule(Manufacturing Example IV-2) | 10 |
| Purified water | 49 |
| Antiseptic | Q.S. |
| Perfume | Q.S. |

(Preparation Method)

Squalane, cetyl isooctanoate and microcrystalline wax were dissolved with heating, and organophilic clay mineral, POE glyceryl triisostearate, antiseptic and perfume were added thereto. The mixture was heated to 70° C., suspended and dissolved uniformly to obtain an oily gel. Glycerin was added to purified water, and heated to 70° C. (water phase). By a homomixer, the oily gel and the water phase were mixed uniformly and, with the microcapsule added thereto, further mixed at room temperature, thereby obtaining a W/O cream.

Compounding Example IV-3 Moisture Gel

| Dipropylene glycol | 7 wt % |
|---|---|
| PEG 1500 | 8 |
| Methyl cellulose | 0.2 |
| POE(15) oleyl ether | 1 |
| Potassium hydroxide | 0.1 |
| Coated microcapsule(Manufacturing Example IV-3) | 5 |
| Purified water | 78.3 |
| Antiseptic | Q.S. |
| Coloring agent | Q.S. |
| Chelating agent | Q.S. |
| Perfume | Q.S. |

(Preparation Method)

The ingredients other than potassium hydroxide were mixed and dissolved uniformly, and potassium hydroxide was added thereto, thereby obtain a moisture gel.

Compounding Example IV-4 Powdery Foundation

| | |
|---|---|
| Talc | 20.3 wt % |
| Mica | 35 |
| Kaoline | 5 |
| Titanium dioxide | 10 |
| Titanium mica | 3 |
| Zinc stearate | 1 |
| Red iron oxide | 1 |
| Yellow iron oxide | 3 |
| Black iron oxide | 0.2 |
| Nylon powder | 5 |
| Squalane | 6 |
| Lanolin acetate | 1 |
| Octyldodecyl myristate | 2 |
| Neopentyl glycol diisooctanoate | 2 |
| Sorbitan monooleate | 0.5 |
| Coated microcapsule(Manufacturing Example IV-1) | 5 |
| Antiseptic, Antioxidant | Q.S. |

(Preparation Method)

After pigments were mixed by a blender, ingredients other than the microcapsule were added thereto, and the mixture was pulverized by a pulverizer. The microcapsule was added to and mixed well with the resulting, and then the mixture was compression-molded, whereby a powdery foundation was obtained.

Compounding Example IV-5 Lipstick

| | |
|---|---|
| Titanium dioxide | 4.5 wt. % |
| Red #201 | 0.5 |
| Red #202 | 2 |
| Red #203 | 0.05 |
| Ceresine | 4 |
| Candelilla wax | 8 |
| Carnauba wax | 2 |
| Caster oil | 25 |
| Isostearic acid diglyceride | 39.95 |
| POE(25) POP(20) 2-tetradecyl ether | 1 |
| Purified water | 5 |
| Glycerin | 2 |
| Propylene glycol | 1 |
| Coated microcapsule(Manufacturing Example IV-2) | 5 |
| UV-absorbing agent | Q.S. |
| Antioxidant | Q.S. |

(Preparation Method)

Titanium dioxide, Red #201 and Red #202 were added to a part of castor oil, and the resulting mixture was subjected to roller processing (pigment part). Red #223 was dissolved in the rest of castor oil (dye part). Purified water, glycerin and propylene glycol were uniformly dissolved at 80° C. (water phase). The other ingredients except for the microcapsule were mixed together, and the pigment part and dye part were added thereto. The mixture was uniformly dispensed by a homomixer and then, with the water phase added thereto, was emulsified by the homomixer. Further, the microcapsule was added and dispensed therein, and then the resulting mixture was caused to flow into a mold and cooled, whereby a lipstick was obtained.

Compounding Example IV-6 Rinse

| | |
|---|---|
| Dimethylpolysiloxane(20 cps) | 3 wt % |
| Liquid paraffin | 1 |
| Cetyl alcohol | 1.5 |

-continued

| | |
|---|---|
| Stearyl alcohol | 1 |
| Stearyl trimethyl ammonium chloride | 0.7 |
| Glycerin | 3 |
| Coated microcapsule(Manufacturing Example IV-3) | 2 |
| Perfume, Coloring agent, Antiseptic | Q.S. |
| Purified water | 87.8 |

(Preparation Method)

Stearyl trimethyl ammonium chloride, glycerin and coloring agent were added to purified water and the mixture was maintained at 70° C. (water phase). The other ingredients except for the microcapsule were dissolved with heating at 70° C., and the microcapsule was added thereto (oil phase). The oil phase was added to the water phase and the mixture was emulsified by a homomixer, and then cooled to obtain a rinse.

What is claimed is:

1. A microcapsule comprising an inner oil phase, a water phase, and an outer oil phase;
   said inner oil phase comprising oil droplets having an average particle size of 0.01 to 3 μm;
   said oil droplets being encapsulated in said water phase;
   said water phase comprising a capsulating agent which is a hydrophilic polymer gelling agent; wherein said hydrophilic polymer gelling agent is agar;
   said water phase being dispersed in said outer oil phase;
   wherein said microcapsule is applied on skin.

2. The microcapsule according to claim 1, wherein a fracture strength of the microcapsule is at least 10 g/cm$^2$ but less than 500 g/cm$^2$.

3. The microcapsule according to claim 2, which releases the encapsulated oil droplet therefrom immediately when the microcapsule is applied on skin.

4. The microcapsule according to claim 1, wherein a fracture strength of the microcapsule is at least 500 g/cm$^2$ but less than 2,000 g/cm$^2$.

5. The microcapsule according to claim 4, which releases the encapsulated oil droplet therefrom gradually when the microcapsule is applied on skin.

6. The microcapsule according to claim 1, wherein a fracture strength of the microcapsule is at least 2,000 g/cm$^2$ but no more than 5000 g/cm$^2$.

7. The microcapsule according to claim 6, which does not release the encapsulated oil droplet therefrom when the microcapsule is applied on skin.

8. The microcapsule according to claim 1, wherein the capsulating agent comprises a hydrophilic polymer gelling agent which hardens by heating and cooling.

9. The microcapsule according to claim 8, wherein the hydrophilic polymer gelling agent is carrageenan.

10. The microcapsule according to claim 1, which comprises a hydrophilic nonionic surfactant and a water-soluble solvent.

11. The microcapsule according to claim 1, wherein said microcapsule is obtained by the steps of:
    preparing an O/W emulsion from the inner oil phase and the water phase containing the hydrophilic polymer gelling agent;
    preparing an O/W/O emulsion by dispersing and emulsifying the O/W emulsion into the outer oil phase; and
    hardening the water phase of the O/W/O emulsion.

12. The microcapsule oily dispersion according to claim 11, wherein the O/W emulsion is prepared by the steps of:
    preparing an oil-in-water-soluble-solvent emulsion by adding the inner oil phase to a water-soluble solvent containing a hydrophilic nonionic surfactant; and adding an aqueous solution of the hydrophilic polymer gelling agent to the oil-in-water-soluble-solvent emulsion.

13. The microcapsule according to claim 1, which is obtained by eliminating the outer oil phase by centrifugation or filtration.

14. The microcapsule according to claim 1, which comprises an oil-soluble drug therein.

15. The microcapsule according to claim 6, which comprises an organic UV-absorbing agent therein.

16. A cosmetic preparation, which comprises the microcapsule according to claim 1.

17. A solid cosmetic preparation, which comprises the microcapsule according to claim 1.

18. A sunscreen cosmetic preparation, which comprises the microcapsule according to claim 15.

19. A coated microcapsule, wherein the microcapsule according to claim 1 is coated with a coating agent.

20. The coated microcapsule according to claim 19, wherein the coating agent is a lipophilic or amphiphilic coating agent.

21. The coated microcapsule according to claim 20, wherein the coating agent is a hydrophobic polysaccharide.

22. The coated microcapsule according to claim 19, wherein the coating agent is a hydrophilic coating agent.

23. A cosmetic preparation, which comprises the coated microcapsule according to claim 19.

24. A method of making a microcapsule for external skin use, which comprises the steps of:

preparing an O/W emulsion from an inner oil phase and a water phase in which a hydrophilic polymer gelling agent hardening by heating and cooling has been dissolved with heating beforehand, at a hardening temperature of the gelling agent or higher, said O/W emulsion having an average particle size of 0.01 to 3 µm;

preparing an O/W/O emulsion by dispersing and emulsifying the O/W emulsion into an outer oil phase at the hardening temperature of the gelling agent or higher; and hardening and capsulating the water phase by cooling the O/W/O emulsion to the hardening temperature of the gelling agent or lower to form said microcapsule;

wherein said microcapsule is applied on skin.

25. The method of making a microcapsule according to claim 24, wherein the step of preparing the O/W emulsion comprises the steps of:

preparing an oil-in-water-soluble emulsion by adding the inner oil phase into a water-soluble solvent containing a hydrophilic nonionic surfactant; and mixing, at the hardening temperature of the gelling agent or higher, the oil-in-water-soluble-solvent emulsion with an aqueous solution in which the hydrophilic polymer gelling agent hardening by heating and cooling has been dissolved with heating beforehand.

26. The method of making a microcapsule according to claim 24, wherein a gel prepared from the water phase has a fracture strength of at least 10 $g/cm^2$ but less than 500 $g/cm^2$.

27. The method of making a microcapsule according to claim 24, wherein a gel prepared from the water phase has a fracture strength of at least 500 $g/cm^2$ but less than 2,000 $g/cm^2$.

28. The method of making a microcapsule according to claim 24, wherein a gel prepared from the water phase has a fracture strength of at least 2,000 $g/cm^2$ but no more than 5,000 $g/cm^2$.

29. The microcapsule according to claim 1, wherein said outer oil phase comprises silicone oil.

30. The microcapsule according to claim 29, wherein said silicone oil is polyoxyethylene (POE) methylpolysiloxane copolymer or dimethylpolysiloxane.

31. The microcapsule according to claim 1, wherein said hydrophilic polymer gelling agent hardens to form a hydrophilic gel by a heating and cooling process.

32. The microcapsule according to claim 1, wherein said inner oil phase and said outer oil phase have different polarity.

* * * * *